US008980884B2

(12) United States Patent
Puglielli

(10) Patent No.: US 8,980,884 B2
(45) Date of Patent: Mar. 17, 2015

(54) METHODS FOR TREATING ALZHEIMER'S DISEASE

(75) Inventor: Luigi Puglielli, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 23 days.

(21) Appl. No.: 13/484,725

(22) Filed: May 31, 2012

(65) Prior Publication Data

US 2012/0329789 A1    Dec. 27, 2012

Related U.S. Application Data

(60) Provisional application No. 61/492,146, filed on Jun. 1, 2011.

(51) Int. Cl.
| | | |
|---|---|---|
| A61K 31/535 | (2006.01) | |
| A61K 31/50 | (2006.01) | |
| A61K 31/00 | (2006.01) | |
| A61K 31/136 | (2006.01) | |
| A61K 31/498 | (2006.01) | |
| A61K 31/538 | (2006.01) | |
| A61K 31/496 | (2006.01) | |

(52) U.S. Cl.
CPC .............. *A61K 31/00* (2013.01); *A61K 31/496* (2013.01); *A61K 31/136* (2013.01); *A61K 31/498* (2013.01); *A61K 31/538* (2013.01)
USPC ..................... 514/228.8; 514/229.8; 514/247; 514/248

(58) Field of Classification Search
CPC ........................... A61K 31/496; A61K 31/498
USPC ............................. 514/228.8, 229.8, 247, 248
See application file for complete search history.

(56) References Cited

U.S. PATENT DOCUMENTS

| | | | |
|---|---|---|---|
| 2009/0117040 | A1 | 5/2009 | Wanker et al. |
| 2009/0136977 | A1 | 5/2009 | Puglielli |

FOREIGN PATENT DOCUMENTS

| | | | |
|---|---|---|---|
| CN | 101830792 | A | 9/2010 |
| EP | 1067386 | A2 | 1/2001 |
| WO | WO 9604915 | A1 * | 2/1996 |
| WO | 03063880 | A1 | 8/2003 |
| WO | 2004099388 | A2 | 11/2004 |
| WO | 2010026592 | A1 | 3/2010 |

OTHER PUBLICATIONS

Viega-Da-Cunha, Maria et al., Molecular Identification of NAT8 as the Enzyme That Acetylates Cysteine S-Conjugates to Mercapturic Acids, Journal of Biological Chemistry, 2010, 285(24):18888-18898 (Jun. 11, 2010; originally published online Apr. 13, 2010).
PCT International Search Report and Written Opinion, PCT/US2012/040123, Nov. 16, 2012.
Bermejo-Bescos, et al., In Vitro Antiamyloidogenic Properties of 1,4-naphthoquinones, Biochemical and Biophysical Research Communications, 2010, 400(1):169-174.
Ding, et al., Biochemical Inhibition of the Acetyltransferases ATase1 and ATase2 Reduces B-Secretase (BACE1) Levels and AB Generation, Journal of Biological Chemistry, 2012, 287(11):8424-8433.
Ko, et al., Identification of ATase1/ATase2 Biochemical Inhibitors that Modulates the Levels of BACE1 and the Generation of AB: A Potential Role for the Treatment of Alzheimer's Disease, Presentation Abstract, Program #599.4, 2009, Neuroscience Meeting Planner, Chicago, IL: Society of Neuroscience, 2009, Online.
Medina, et al., Methylene Blue Reduces AB Levels and Rescues Early Cognitive Deficit by Increasing Proteasome Activity, Brain Pathology, 2011, 21:140-149.
Taniguchi, et al., Inhibition of Heparin-induced Tau Filament Formation by Phenothiazines, Polyphenols, and Porphyrins, Journal of Biological Chemistry, 2005, 280(9):7614-7623.
Agarwal, et al., Quinone Chemistry. Reaction of 2,3-dichloro--1,4-napthoquinone with o-aminophenols Under Various Conditions, Journal oOrganic Chemistry, 1980, 45(11):2155-2161.
Agarwal, et al., Quinone Chemistry. Reaction of 2,3-dichloro-1,4-naphthoquinone with 2-aminophenols in Pyridine, Journal of Organic Chemistry, 1980, 45(25):5144-5149.
Cai, et al., BACE1 is the Major B-Secretase for Generation of AB Peptides by Neurons, Nature Neuroscience, 2001, 4(3):233-234.
Cleary, et al., Natural Oligomers of the Amyloid-B Protein Specifically Disrupt Cognitive Function, Nature Neuroscience, 2005, 8(1):79-84.

(Continued)

*Primary Examiner* — Kevin E Weddington
(74) *Attorney, Agent, or Firm* — Quarles & Brady LLP

(57) ABSTRACT

Pharmaceutical compositions for treating Alzheimer's disease are disclosed. The pharmaceutical compositions include a compound having the general formula:

and a pharmaceutically acceptable carrier. Methods for treating Alzheimer's disease, inhibiting ATase I and/or ATase 2, reducing the activity of BACE1, reducing the level of amyloid β-peptide (Aβ), and/or reducing the level of APP intracellular domain peptide (AICD) by administering such compositions are also disclosed.

2 Claims, 18 Drawing Sheets

(56) References Cited

OTHER PUBLICATIONS

Costantini, et al., A Reversible Form of Lysine Acetylation in the ER and Golgi Lumen Controls the Molecular Stabilization of BACE1, Biochem J., 2007, 407:383-395.

Ghosal, et al., Alzheimer's Disease-like Pathological Features in Transgenic Mice Expressing the APP Intracellular Domain, Proc. Natl. Acad. Sci. USA, 2009, 106(43):18367-18372.

Giliberto, et al., Evidence that the Amyloid Beta Precursor Protein-intracellular Domain Lowers the Stress Threshold of Neurons and has a "Regulated" Transcriptional Role, Molecular Neurodegeneration, 2008, 3:12, 12 pages.

Haass, et al., Protofibrils, the Unifying Toxic Molecule of Neurodegenerative Disorders?, Nature Neuroscience, 2001, 4:859-860.

Jonas, et al., PCSK9 is Required for the Disposal of Non-Acetylated Intermediates of the Nascent Membrane Protein BACE1, EMBO Reports, 2008, 9(9):916-922.

Jonas, et al., AT-1 is the ER Membrane Acetyl-CoA Transporter and is Essential for Cell Viability, Journal of Cell Science, 2010, 123:3378-3388.

Ko, et al., The Sterol Carrier Protein SCP-x/Pro-SCP-2 Gene Has Transcriptional Activity and Regulates the Alzheimer Disease y-Secretase, Journal of Biological Chemistry, 2007, 282(27):19742-19752.

Ko, et al., Two Endoplasmic Reticulum (ER)/ER Golgi Intermediate Compartment-Based Lysine Acetyltransferases Post-Translationally Regulate BACE1 Levels, Journal of Biological Chemistry, 2009, 284(4):2482-2492.

Lambert, et al., Diffusible, Nonfibrillar Ligands Derived from AB1-42 Are Potent Central Nervous System Neurotoxins, Proc. Natl. Acad. Sci. USA, 1998, 95:6448-6453.

Lansbury, Evolution of Amyloid: What Normal Protein Folding May Tell Us About Fibrillogenesis and Disease, Proc. Natl. Acad. Sci. USA, 1999, 96:3342-3344.

Luo, et al., Mice Deficient in BACE1, the Alzheimer's B-secretase, Have Normal Phenotype and Abolished B-amyloid Generation, Nature Neuroscience, 2001, 4(3):231-232.

Puglielli, Aging of the Brain, Neurotrophin Signaling, and Alzheimer's Disease: Is IGF1-R the Common Culprit?, Neurobiol. Aging, 2008, 29(6):795-811.

Puzzo, et al., Picomolar Amyloid-B Positively Modulates Synaptic Plasticity and Memory in Hippocampus, Journal of Neuroscience, 2008, 28(53):14537-14545.

\* cited by examiner

9

9.H

9.I

9.J

9.K

9.L

9.M

19.A

19.B

19.C

Chemical Formula: $C_{17}H_{20}ClNO_6^{2+}$
Exact Mass (predicted): 369.10
Exact Mass (measured): 369.4
Molecular Weight: 369.80

Chemical Formula: $C_{17}H_{20}ClNO_6^{2+}$
Exact Mass (predicted): 369.10
Exact Mass (measured): 369.4
Molecular Weight: 369.80

Chemical Formula: $C_{17}H_{20}ClNO_6{}^{2+}$
Exact Mass (predicted): 369.10
Exact Mass (measured): 369.4
Molecular Weight: 369.80

METHODS FOR TREATING ALZHEIMER'S DISEASE

CROSS REFERENCE TO RELATED APPLICATIONS

This application claims the benefit of U.S. Provisional Application No. 61/492,146, filed on Jun. 1, 2011, which is incorporated by reference herein.

STATEMENT OF GOVERNMENT SUPPORT

This invention was made with government support under NS045669 and AG033514 awarded by the National Institutes of Health. The government has certain rights in the invention.

BACKGROUND

The membrane protein β-site APP cleaving enzyme 1 (BACE1) is responsible for the β cleavage of the amyloid precursor protein (APP). The cleavage, which has been linked to the pathogenesis of Alzheimer's disease (AD), results in the generation of a small APP fragment (commonly referred to as C99) acting as the immediate substrate for γ secretase (Puglielli, 2008). The sequential β/γ processing of APP results into two small fragments, the amyloid β-peptide (Aβ) and the APP intracellular domain (AICD). Both have neurotoxic properties and both have been linked to the pathogenesis of AD (Cleary et al., 2005; Ghosal et al., 2009; Giliberto et al., 2008; Haass and Steiner, 2001; Klein et al., 2001; Lambert et al., 1998; Lansbury, 1999; Puzzo et al., 2008). BACE1 acts as the rate-limiting enzyme for these processing steps. As a result, genetic disruption of BACE1 in the mouse abolishes both β and γ cleavage of APP and prevents AD neuropathology (Cai, 2001; Luo, 2001). Therefore, mechanisms that regulate levels and activity of BACE1 could be effective targets for the development of therapeutic agents.

We recently reported that nascent BACE1 is transiently acetylated on seven lysine residues in the lumen of the ER (Costantini, 2007) by two ER-based acetyl-CoA:lysine acetyltransferases which we named ATase1 (also known as camello-like 2 and N-acetyltransferase 8B) and ATase2 (also known as camello-like 1 and N-acetyltransferase 8) (Ko and Puglielli, 2009). The Nε-lysine acetylation regulates the ability of nascent BACE1 to complete maturation. In fact, the acetylated intermediates of the nascent protein are able to reach the Golgi apparatus and complete maturation while the non-acetylated intermediates are retained and degraded in the ER Golgi intermediate compartment (ERGIC) (Costantini, 2007; Jonas, 2008). Ex vivo studies show that the levels of BACE1 are tightly regulated by the ATases. In fact, up-regulation of ATase1 and ATase2 increases the levels of BACE1 and the generation of Aβ while siRNA-mediated down-regulation of either transferase achieves the opposite effects (Ko and Puglielli, 2009).

SUMMARY

The present inventors have identified biochemical inhibitors of ATase1 and ATase2 that significantly reduce the levels of BACE1 and the generation of Aβ in cellular systems and in an animal model of AD. The experiments described herein confirm that the disclosed inhibitors can be effectively used for the prevention and/or treatment of AD.

In a first aspect, the disclosure encompasses a pharmaceutical composition that includes a pharmaceutically acceptable carrier and a compound of Formula I or Formula II, as set forth below.

In some embodiments, the composition comprises a compound selected from compounds of Formula I:

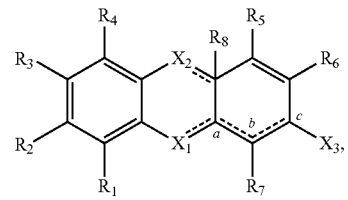

and pharmaceutically acceptable salts thereof. In some embodiments, $R_1$, $R_2$, $R_3$, $R_4$, and $R_7$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl, wherein $R_9$ and $R_{10}$ are independently selected from $C_1$-$C_5$ alkyl. In some embodiments, $R_8$ is selected from hydrogen, halogen, —OH, —$NH_2$, and —SH, or is absent. In some embodiments, $R_5$ and $R_6$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl, wherein $R_9$ and $R_{10}$ are independently selected from $C_1$-$C_5$ alkyl. In some embodiments, $R_5$ and $R_6$ together are

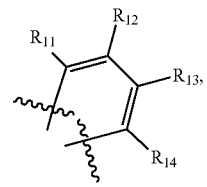

wherein $R_{11}$, $R_{12}$, $R_{13}$, and $R_{14}$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl, wherein $R_9$ and $R_{10}$ are independently selected from $C_1$-$C_5$ alkyl. In some embodiments, $X_1$ is selected from N, NH, O, and S. In some embodiments, $X_2$ is selected from N, O, and S. In some embodiments, $X_3$ is selected from —OH, =O, —$NH_2$, =NH, —SH, and =S. In some embodiments, the $X_1$ to carbon a ($C_a$) bond and the carbon b ($C_b$) to carbon c ($C_c$) bond are both double bonds, or the $C_a$ to $C_b$ bond is a double bond.

In some embodiments, $R_1$, $R_3$, $R_4$, and $R_7$ are each independently selected from hydrogen and halogen. In some embodiments, $R_1$, $R_3$, and $R_4$ are each hydrogen and $R_7$ is halogen. In some embodiments, $R_5$ and $R_6$ are each independently selected from hydrogen, halogen, and methyl. In some embodiments, $R_5$ and $R_6$ together are

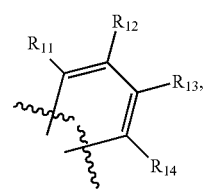

wherein $R_{11}$, $R_{12}$, $R_{13}$, and $R_{14}$ are each independently selected from hydrogen and halogen. In some embodiments, $R_5$ and $R_6$ are each hydrogen or halogen. In some embodiments, $R_5$ and $R_6$ together are

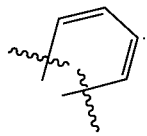 [SMILES: */C=C\C=C/*]

In some embodiments, $R_2$ is selected from hydrogen, halogen, —OH, —OR$_9$, —SH, —SR$_9$, —NH$_2$, —NHR$_9$, —NR$_9$R$_{10}$, and $C_1$-$C_6$ alkyl, wherein $R_9$ and $R_{10}$ are independently selected from $C_1$-$C_3$ alkyl. In some embodiments, $R_8$ is selected from hydrogen, halogen, —OH, and —SH, or is absent. In some embodiments, $X_2$ is N and $R_8$ is absent. In some embodiments, $X_2$ is O and $R_8$ is selected from hydrogen, halogen, —OH, and —SH.

In some embodiments, the compound is selected from the compounds in Table 1, and pharmaceutically acceptable salts thereof.

In some embodiments, a pharmaceutical composition comprises a compound selected from compounds of Formula II:

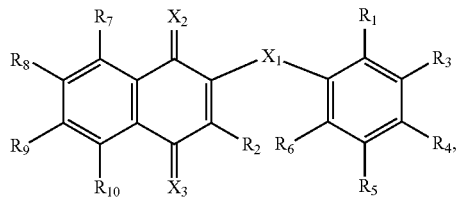

and pharmaceutically acceptable salts thereof.

In some embodiments, $R_1$ is selected from hydrogen, halogen, —OH, —OR$_{11}$, —SH, —SR$_{11}$, —NH$_2$, —NHR$_{11}$, —NR$_{11}$R$_{12}$, and $C_1$-$C_{10}$ alkyl, wherein $R_{11}$ and $R_{12}$ are independently selected from $C_1$-$C_6$ alkyl. In some embodiments, $R_2$ is selected from hydrogen, halogen, —OH, —SH, and —NH3. In some embodiments, $R_3$ to $R_{10}$ are each independently selected from hydrogen, halogen, —OH, —OR$_{11}$, —SH, —SR$_{11}$, —NH$_2$, —NHR$_{11}$, —NR$_{11}$R$_{12}$, and $C_1$-$C_{10}$ alkyl, wherein $R_{11}$ and $R_{12}$ are independently selected from $C_1$-$C_6$ alkyl. In some embodiments, $X_1$ is selected from O, S, and NH. In some embodiments, $X_2$ and $X_3$ are each independently selected from O, S, and NH.

In some embodiments, $R_3$ to $R_{10}$ are each independently selected from hydrogen, halogen, —OH, —OR$_{11}$, —SH, —SR$_{11}$, —NH$_2$, —NHR$_{11}$, —NR$_{11}$R$_{12}$, and $C_1$-$C_{10}$ alkyl, wherein $R_{11}$ and $R_{12}$ are independently selected from $C_1$-$C_3$ alkyl. In some embodiments, $R_3$ to $R_{10}$ are each independently selected from hydrogen and halogen. In some embodiments, $R_1$ is selected from hydrogen, halogen, —OH, —OR$_{11}$, —SH, —SR$_{11}$, —NH$_2$, —NHR$_{11}$, —NR$_{11}$R$_{12}$, and $C_1$-$C_{10}$ alkyl, wherein $R_{11}$ and $R_{12}$ are independently selected from $C_1$-$C_4$ alkyl. In some embodiments, $R_1$ is selected from hydrogen, halogen, —OH, —OR$_{11}$, —SH, —SR$_{11}$, —NH$_2$, —NHR$_{11}$, —NR$_{11}$R$_{12}$, and $C_1$-$C_{10}$ alkyl, wherein $R_{11}$ and $R_{12}$ are independently selected from $C_1$-$C_3$ alkyl. In some embodiments, $R_2$ is selected from hydrogen and halogen. In some embodiments, $X_1$ is NH. In some embodiments, $X_2$ and $X_3$ are each O.

In some embodiments, the compound is selected from the compounds in Table 2, and pharmaceutically acceptable salts thereof.

In a second aspect, the disclosure encompasses methods of treating, slowing the progression of, delaying the onset of, or alleviating at least one symptom of Alzheimer's disease. In some embodiments, the at least one symptom is selected from memory loss, confusion, impaired judgment, disorientation, and loss of language skills. In some embodiments, the method comprises administering to a patient a pharmaceutical composition comprising an inhibitor of ATase1 and/or ATase2. In some embodiments, the method comprises administering to a patient a pharmaceutical composition comprising a compound selected from the compounds of Formula I and II, and pharmaceutically acceptable salts thereof.

In a third aspect, the disclosure encompasses methods of inhibiting at least one acetyltransferase selected from ATase 1 and ATase 2 in a cell, reducing the activity of β-site APP cleaving enzyme 1 (BACE1) in a cell, or reducing the level of APP intracellular domain peptide (AICD) in a cell. In some embodiments, the method comprises contacting the cell with a pharmaceutical composition comprising a compound selected from the compounds of Formula I and II, including without limitation the specific compounds disclosed in Table 1 and Table 2 below, and pharmaceutically acceptable salts thereof. In some embodiments, the cell is in vitro. In some embodiments, the cell is in vivo.

In a fourth aspect, the disclosure encompasses the compounds of Formula I and Formula II, including without limitation the specific compounds disclosed in Table 1 and Table 2 below, for use in treating Alzheimer's disease.

In a fifth aspect, the disclosure encompasses the compounds of Formula I and Formula III, including without limitation the specific compounds disclosed in Table 1 and Table 2 below, for use in the manufacture of a medicament for treating Alzheimer's disease.

DETAILED DESCRIPTION

Figure 1:
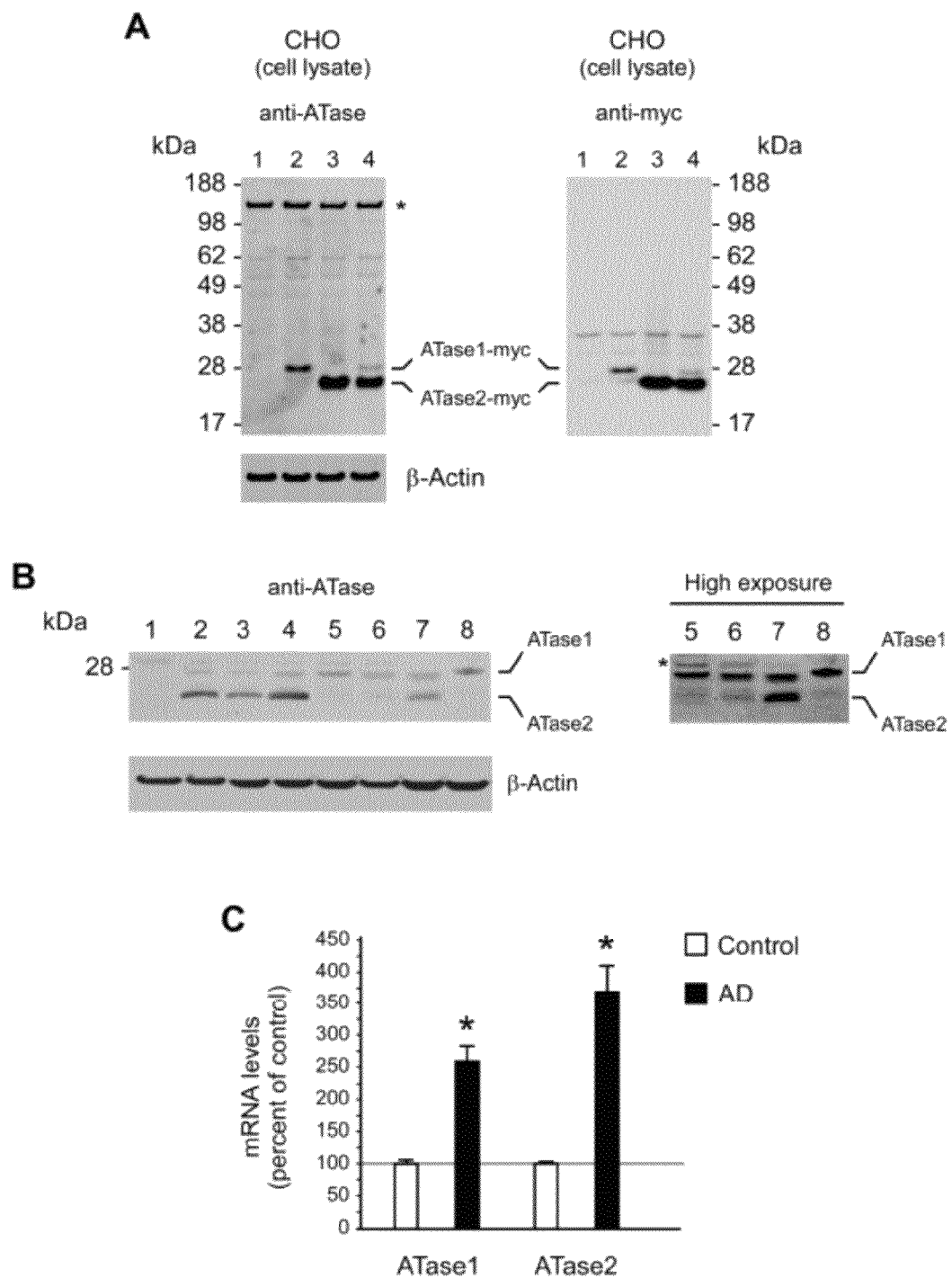
FIG. 1. ATase1 and ATase2 are expressed in neurons and are up-regulated in the brain of AD patients. (A) Western blot assessment of CHO cells over-expressing human ATase1 and/or ATase2. The left panel was generated with an anti-ATase1/ATase2 antibody while the right panel was generated with an anti-myc antibody. Lane 1, control (untransfected) cells; lane 2, stable over-expression of ATase1; lane 3, stable over-expression of ATase2; lane 4, stable over-expression of both ATase1 and ATase2. (B) Western blot showing the endogenous levels of ATase1 and ATase2 in different cellular systems. The right panel shows higher exposure of the same image. Lane 1, CHO cells; lane 2, H4 cells; lane 3, SH-SY5Y cells; lane 4, SHEP cells; lane 5, PC-12 cells; lane 6, primary neurons (day 3 in culture); lane 7, primary neurons (day 18 in culture); lane 8; whole brain extract (cortex). Asterisks (*) indicates a background band that migrates immediately above the 28-kDa marker. (C) cDNA produced from brain tissue (frontal cortex) of late-onset AD patients (n=5; average age: 87; age range: 85-93) and age-matched controls (n=5; average age: 88; age range: 86-91) was analyzed by quantitative real-time PCR. Results were normalized against GAPDH and are expressed as percent of age-matched controls ±s.e.m. **, P<0.005.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. Molecular Cloning: A Laboratory Manual (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

The section headings used herein are for organizational purposes only and are not to be construed as limiting the subject matter described.

DEFINITIONS

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the term "inhibitor of ATase1 and/or ATase2" refers to a molecule that interacts with ATase1 and/or ATase2 and reduces the activity of ATase1 and/or ATase2 by at least 30% according to an assay described herein. In some embodiments, an inhibitor of ATase1 and/or ATase2 reduces the activity of ATase1 and/or ATase2 by at least 40%, at least 50%, at least 60%, at least 70%, at least 80%, or at least 90%. In some embodiments, an inhibitor of ATase1 and/or ATase2 is a small molecule. In some embodiments, an inhibitor of ATase1 and/or ATase2 is a compound selected from the compounds of Formula I and Formula II, and pharmaceutically acceptable salts thereof. Inhibitors of ATase1 and/or ATase2 include inhibitors of ATase1, inhibitors of ATase2, and inhibitors of ATase1 and ATase 2.

As used herein, the term "inhibitor of ATase1" refers to a molecule that interacts with ATase1 and reduces the activity of ATase1 by at least 30% according to an assay described herein. In some embodiments, an inhibitor of ATase1 reduces the activity of ATase1 by at least 40%, at least 50%, at least 60%, at least 70%, at least 80%, or at least 90%. In some embodiments, an inhibitor of ATase1 is a small molecule. In some embodiments, an inhibitor of ATase1 is a compound selected from the compounds of Formula I and Formula II, and pharmaceutically acceptable salts thereof.

As used herein, the term "inhibitor of ATase2" refers to a molecule that interacts with ATase2 and reduces the activity of ATase2 by at least 30% according to an assay described herein. In some embodiments, an inhibitor of ATase2 reduces the activity of ATase2 by at least 40%, at least 50%, at least 60%, at least 70%, at least 80%, or at least 90%. In some embodiments, an inhibitor of ATase2 is a small molecule. In some embodiments, an inhibitor of ATase2 is a compound selected from the compounds of Formula I and Formula II, and pharmaceutically acceptable salts thereof.

As used herein, the term "inhibitor of ATase1 and ATase2" refers to a molecule that interacts with both ATase1 and ATase2 and reduces the activity of each of ATase1 and ATase2 by at least 30% according to an assay described herein. In some embodiments, an inhibitor of ATase1 and ATase2 reduces the activity of each of ATase1 and ATase2 by at least 40%, at least 50%, at least 60%, at least 70%, at least 80%, or at least 90% (although it may not reduce the activity of ATase1 and ATase2 to the same extent). In some embodiments, an inhibitor of ATase1 and ATase2 is a small molecule. In some embodiments, an inhibitor of ATase1 and ATase2 is a compound selected from the compounds of Formula I and Formula II, and pharmaceutically acceptable salts thereof.

The terms "patient" and "subject" are used interchangeably to refer to a refer to one who receives medical care, attention or treatment. As used herein, the term is meant to encompass a person diagnosed with a disease such as a Alzheimer's disease or at risk for developing Alzheimer's disease. A "patient in need thereof" may include a patient having, suspected of having, or at risk for developing Alzheimer's disease or symptoms thereof.

As used herein, the term "treatment," "treating," or "treat" refers to care by procedures or application that are intended to alleviate a disease or symptoms of a disease (including reducing the occurrence of symptoms of the disease). Although it is preferred that treating a condition or disease such as Alzheimer's disease will result in an improvement of the condition or disease, the term treating as used herein does not indicate, imply, or require that the procedures or applications are always successful in treating the condition disease or alleviating symptoms associated with the condition or disease. Treating a patient may result in adverse side effects or, in some instances, even a worsening of the condition which the treatment was intended to improve. Treating may include treating a patient having, suspected of having, or at risk for developing Alzheimer's disease or symptoms thereof. In some embodiments, treating Alzheimer's disease results in a reduction in the amount of Aβ peptide in the brain and/or a reduction in the number and/or size of amyloid plaques.

As used herein, the term "prevention," "preventing," or "prevent" refers to care by procedures or application that are intended to inhibit or stop development of a disease or symptoms of a disease (including inhibiting or stopping the occurrence of symptoms of the disease). Although it is preferred that preventing a condition or disease such as Alzheimer's disease will result in a failure of the condition or disease to develop, the term preventing as used herein does not indicate, imply, or require that the procedures or applications are always successful in inhibiting development of the condition or disease or symptoms associated with the condition or disease. Preventing a condition or disease may result in adverse side effects or, in some instances, even a worsening of the condition or disease that the treatment was intended to prevent. Methods of preventing a condition or disease may include treating a patient suspected of having, or at risk for developing Alzheimer's disease or symptoms thereof. In some embodiments, preventing Alzheimer's disease means that elevated levels of Aβ peptide are not formed and/or amyloid plaques are not formed in the brain.

As used herein, the term "slowing the progression of" or "slows the progression of" refers to care by procedures or application that are intended to reduce the rate of development of a disease or symptoms of a disease (including reducing the rate of occurrence of symptoms of the disease). Although it is preferred that slowing the progression of a condition or disease such as Alzheimer's disease will result in a reduction in the rate that the condition or disease develops, the term "slowing the progression of" as used herein does not indicate, imply, or require that the procedures or applications are always successful in slowing the rate of development of the condition or disease or symptoms associated with the condition or disease. Slowing the progression of a condition or disease may result in adverse side effects or, in some instances, even a worsening of the condition or disease that the treatment was intended to slow. Methods of slowing the progression of a condition or disease may include treating a patient having, suspected of having, or at risk for developing Alzheimer's disease or symptoms thereof. In some embodiments, slowing the progression of Alzheimer's disease results in a reduction in the rate of formation of Aβ peptide in the brain and/or a reduction in rate of formation of amyloid plaques (the number and/or size of amyloid plaques).

As used herein, the term "delaying the onset of" or "delays the onset of" refers to care by procedures or application that are intended to delay in time the development of a disease or symptoms of a disease (including delaying in time the appearance or occurrence of symptoms of the disease). Although it is preferred that delaying the onset of a condition or disease such as Alzheimer's disease will result in a delay in time before the condition or disease develops, the term "delaying the onset of" as used herein does not indicate, imply, or require that the procedures or applications are always successful in delaying the onset of the condition or disease or symptoms associated with the condition or disease. Delaying the onset of a condition or disease may result in adverse side effects or, in some instances, even a worsening of the condition or disease that the treatment was intended to delay. Methods of delaying the onset of a condition or disease may include treating a patient suspected of having, or at risk for developing Alzheimer's disease or symptoms thereof. In some embodiments, delaying the onset of Alzheimer's disease results in a reduction in the rate of formation of Aβ peptide in the brain and/or a reduction in rate of formation of amyloid plaques (the number and/or size of amyloid plaques).

As used herein the term "effective amount" refers to the amount or dose of the agent, upon single or multiple dose administration to the subject, which provides the desired effect in the subject under diagnosis or treatment. The disclosed methods may include administering an effective amount of the disclosed compounds (e.g., as present in a pharmaceutical composition) for treating Alzheimer's disease in the patient, whereby the effective amount alleviates a molecular cause or symptom of Alzheimer's disease (including reducing the occurrence of such causes or symptoms of Alzheimer's disease).

An effective amount can be readily determined by the attending diagnostician, as one skilled in the art, by the use of known techniques and by observing results obtained under analogous circumstances. In determining the effective amount or dose of agent administered, a number of factors can be considered by the attending diagnostician, such as: the species of the patient; its size, age, and general health; the particular symptoms or the severity of the disease; the response of the individual patient; the particular agent administered; the mode of administration; the bioavailability characteristics of the preparation administered; the dose regimen selected; the use of concomitant medication; and other relevant circumstances.

The phrase "alleviates at least one symptom," as used herein, means that a particular treatment results in a lessening of at least one symptom of a disease. Such lessening of a symptom may be a qualitative or quantitative reduction in the severity of the symptom, or may be a reduction in the number of occurrences of the symptom, even though each occurrence may be as severe as it was before the treatment (one or more occurrences may also be less severe). Nonlimiting exemplary symptoms of Alzheimer's disease include memory loss, confusion, impaired judgment, disorientation, and loss of language skills.

Exemplary Methods

In some embodiments, methods of treating Alzheimer's disease are provided. In some embodiments, methods of alleviating at least one symptom thereof are provided. In some embodiments, the at least one symptom is selected from memory loss, confusion, impaired judgment, disorientation, and loss of language skills. In some embodiments, methods of preventing Alzheimer's disease are provided. In some embodiments, methods of slowing the progression of Alzheimer's disease are provided. In some embodiments, methods of delaying the onset of Alzheimer's disease are provided.

In some embodiments, a method comprises administering to a patient an inhibitor of ATase1 and/or ATase2. In some embodiments, a method comprises administering to a patient a compound selected from the compounds of Formula I and pharmaceutically acceptable salts thereof and/or a compound selected from the compounds of Formula II and pharmaceutically acceptable salts thereof. In some embodiments, a method comprises administering to a patient a compound selected from the compounds in Tables 1 and 2 below and pharmaceutically acceptable salts thereof. In some embodiments, the compound is comprised in a pharmaceutical composition suitable for administration to a patient.

Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections. Further, a pharmaceutical composition can be delivered locally, for example, by direct injection into a specific tissue.

For any compounds of the present invention, the therapeutically effective dose can be estimated initially from in vitro assays or using art-recognized animal model systems or a combination thereof. For example, a dose can be formulated in animal models to achieve a circulating concentration range that includes the EC50 (effective dose for 50% decrease) as determined in vitro, i.e., the concentration of the test compound which achieves a half-maximal reduction in ATase1 and/or ATase 2 activity. Such information can be used to more accurately determine useful doses in humans.

It will be understood, however, that the specific dose level for any particular patient will depend upon a variety of factors including the activity of the compounds employed, body weight, general health, sex, diet, time of administration, route of administration, and rate of excretion, and other drugs currently taken by the patient.

In some embodiments, methods of inhibiting at least one acetyltransferases selected from ATase 1 and ATase 2 in a cell are provided. In some embodiments, methods of reducing the activity of β-site APP cleaving enzyme 1 (BACE1) in a cell are provided. In some embodiments, methods of reducing the level of amyloid β-peptide (Aβ) in a cell are provided. In some embodiments, methods reducing the level of APP intracellular domain peptide (AICD) in a cell are provided.

In some embodiments, such methods comprise contacting the cell with a compound selected from the compounds of Formula I and pharmaceutically acceptable salts thereof and/or a compound selected from the compounds of Formula II and pharmaceutically acceptable salts thereof. In some embodiments, the compound is selected from the compounds in Table 1 and Table 2, and pharmaceutically acceptable salts thereof. The cell may be in vitro or may be in vivo (i.e., may be comprised within an organism, such as a human patient). In some embodiments in which the cell is comprised in a patient, the method comprises administering the compound to the patient. Cells in vitro may be in the form of dissociated cells, cells in suspension culture, cells in monolayer culture, cells in 3D culture, cells comprised in ex vivo tissues, cells comprised in ex vivo organs, and the like.

Exemplary Compounds and Pharmaceutical Compositions

In some embodiments, compounds of Formula I and pharmaceutically acceptable salts thereof are provided:

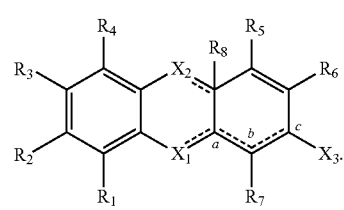

I

In some embodiments, $R_1$, $R_2$, $R_3$, $R_4$, and $R_7$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl. In some embodiments, $R_1$, $R_2$, $R_3$, $R_4$, and $R_7$ are each independently selected from hydrogen, halogen, —OH, —$OR_9$, —SH, —$SR_9$, —$NH_2$, —$NHR_9$, —$NR_9R_{10}$, and $C_1$-$C_8$ alkyl. In some embodiments, $R_1$, $R_2$, $R_3$, $R_4$, and $R_7$ are each independently selected from hydrogen, halogen, —OH, —$OR_9$, —SH, —$SR_9$, —$NH_2$, —$NHR_9$, —$NR_9R_{10}$, and $C_1$-$C_6$ alkyl. In some embodiments, $R_1$, $R_2$, $R_3$, $R_4$, and $R_7$ are each independently selected from hydrogen, halogen, —OH, —$OR_9$, —SH, —$SR_9$, —$NH_2$, —$NHR_9$, —$NR_9R_{10}$, and $C_1$-$C_6$ alkyl. In some embodiments, $R_9$ and $R_{10}$ are independently selected from $C_1$-$C_5$ alkyl. In some embodiments, $R_9$ and $R_{10}$ are independently selected from $C_1$-$C_4$ alkyl. In some embodiments, $R_9$ and $R_{10}$ are independently selected from $C_1$-$C_3$ alkyl. In some embodiments, $R_9$ and $R_{10}$ are independently selected from $C_1$-$C_2$ alkyl. In some embodiments, $R_1$, $R_3$, $R_4$, and $R_7$ are each independently selected from hydrogen and halogen. In some embodiments, $R_1$, $R_3$, and $R_4$ are each hydrogen and $R_7$ is halogen. In some embodiments, $R_1$, $R_3$, $R_4$, and $R_7$ are hydrogen.

In some embodiments, $R_2$ is selected from hydrogen, halogen, —OH, —$OR_9$, —SH, —$SR_9$, —$NH_2$, —$NHR_9$, —$NR_9R_{10}$, and $C_1$-$C_6$ alkyl. In some such embodiments, $R_9$ and $R_{10}$ are independently selected from $C_1$-$C_3$ alkyl. In some such embodiments, $R_1$, $R_3$, $R_4$, and $R_7$ are each independently selected from hydrogen and halogen. In some such embodiments, $R_1$, $R_3$, and $R_4$ are hydrogen, and $R_7$ is halogen.

In some embodiments, $R_8$ is selected from hydrogen, halogen, —OH, —$NH_2$, and —SH. In some embodiments, $R_8$ is selected from hydrogen, halogen, —OH, and —SH. In some embodiments, for example when the bond connecting $X_2$ to the carbon shared by $X_2$ and $R_8$ is a double bond, $R_8$ is absent.

In some embodiments, $R_5$ and $R_6$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl. In some embodiments, $R_5$ and $R_6$ are each independently selected from hydrogen, halogen, —OH, —$OR_9$, —SH, —$SR_9$, —$NH_2$, —$NHR_9$, —$NR_9R_{10}$, and $C_1$-$C_8$ alkyl. In some embodiments, $R_5$ and $R_6$ are each independently selected from hydrogen, halogen, —OH, —$OR_9$, —SH, —$SR_9$, —$NH_2$, —$NHR_9$, —$NR_9R_{10}$, and $C_1$-$C_6$ alkyl. In some embodiments, $R_5$ and $R_6$ are each independently selected from hydrogen, halogen, —OH, —$OR_9$, —SH, —$SR_9$, —$NH_2$, —$NHR_9$, —$NR_9R_{10}$, and $C_1$-$C_4$ alkyl. In some embodiments, $R_9$ and $R_{10}$ are independently selected from $C_1$-$C_5$ alkyl. In some embodiments, $R_9$ and $R_{10}$ are independently selected from $C_1$-$C_4$ alkyl. In some embodiments, $R_9$ and $R_{10}$ are independently selected from $C_1$-$C_3$ alkyl. In some embodiments, $R_9$ and $R_{10}$ are independently selected from $C_1$-$C_2$ alkyl. It is to be understood that each $R_9$ and $R_{10}$ is independently selected for each $R_1$, $R_2$, $R_3$, $R_4$, $R_5$, $R_6$, $R_7$, etc., that comprises an $R_9$ and/or an $R_{10}$. Thus, for example, in some embodiments, an $R_9$ on an $R_1$ substituent need not be the same as an $R_9$ on an $R_2$ substituent in the same compound.

In some embodiments, $R_5$ and $R_6$ together are

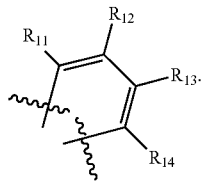

In some such embodiments, $R_{11}$, $R_{12}$, $R_{13}$, and $R_{14}$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl. In some such embodiments, $R_{11}$, $R_{12}$, $R_{13}$, and $R_{14}$ are each independently selected from hydrogen, halogen, —OH, —$OR_9$, —SH, —$SR_9$, —$NH_2$, —$NHR_9$, —$NR_9R_{10}$, and $C_1$-$C_8$ alkyl. In some such embodiments, $R_{11}$, $R_{12}$, $R_{13}$, and $R_{14}$ are each independently selected from hydrogen, halogen, —OH, —$OR_9$, —SH, —$SR_9$, —$NH_2$, —$NHR_9$, —$NR_9R_{10}$, and $C_1$-$C_6$ alkyl. In some such embodiments, $R_{11}$, $R_{12}$, $R_{13}$, and $R_{14}$ are each independently selected from hydrogen, halogen, —OH, —$OR_9$, —SH, —$SR_9$, —$NH_2$, —$NHR_9$, —$NR_9R_{10}$, and $C_1$-$C_4$ alkyl. In some embodiments, $R_9$ and $R_{10}$ are independently selected from $C_1$-$C_5$ alkyl. In some embodiments, $R_9$ and $R_{10}$ are independently selected from $C_1$-$C_3$ alkyl. It is to be understood that each $R_9$ and $R_{10}$ is independently selected for each substituent that comprises an $R_9$ and/or $R_{10}$. In some such embodiments, $R_{11}$, $R_{12}$, $R_{13}$, and $R_{14}$ are each independently selected from hydrogen and halogen. In some embodiments, $R_{11}$, $R_{12}$, $R_{13}$, and $R_{14}$ are hydrogen.

In some embodiments, $R_5$ and $R_6$ are each independently selected from hydrogen, halogen, and methyl. In some embodiments, $R_5$ and $R_6$ together are

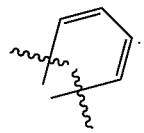 [SMILES: */C=C\C=C/*]

In some embodiments, $X_1$ is selected from N, NH, O, and S. That is, in some embodiments, when $X_1$ is N, the $X_1$ to carbon a ($C_a$) bond is a double bond. In some such embodiments, the carbon b ($C_b$) to carbon c ($C_c$) bond is also a double bond. In some embodiments, when $X_1$ is NH, O, or S, the $C_a$ to $C_b$ bond is a double bond.

In some embodiments, $X_2$ is selected from N, O, and S. In some embodiments, when $X_2$ is N, $R_8$ is absent, and the bond between $X_2$ and the carbon to which $R_8$ is shown attached in Formula I is a double bond. In some embodiments, $X_2$ is O and $R_8$ is selected from hydrogen, halogen, —OH, and —SH.

In some embodiments, $X_3$ is selected from —OH, =O, —$NH_2$, =NH, —SH, and =S.

In some embodiments, a compound of Formula I is provided, wherein $X_1$ is O; $X_2$ is N; $X_3$ is selected from =O, =S, and =NH; the carbon a ($C_a$) to carbon b ($C_b$) bond is a double bond; $R_8$ is absent; $R_1$, $R_3$, $R_4$, and $R_7$ are each independently selected from H and halogen; $R_2$ is selected from hydrogen, halogen, —OH, —$OR_9$, —SH, —$SR_9$, —NH2, —$NHR_9$, —$NR_9R_{10}$, and $C_1$ to $C_6$ alkyl, wherein $R_9$ and $R_{10}$ are each independently selected from $C_1$ to $C_4$ alkyl; and $R_5$ and $R_6$ are together are

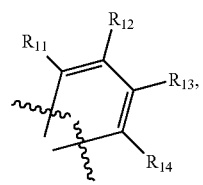

wherein $R_{11}$, $R_{12}$, $R_{13}$, and $R_{14}$ are each independently selected from hydrogen and halogen. In some such embodiments, $R_2$ is selected from hydrogen, halogen, —OH, —$OR_9$, —SH, —$SR_9$, —NH2, —$NHR_9$, —$NR_9R_{10}$, and $C_1$ to $C_4$ alkyl, wherein $R_9$ and $R_{10}$ are each independently selected from $C_1$ to $C_3$ alkyl.

In some embodiments, a compound of Formula I is provided, wherein $X_1$ is N; $X_2$ is N; $X_3$ is selected from —OH, —SH, and —NH$_2$; the $X_1$ to carbon a ($C_a$) bond is a double bond and the carbon b ($C_b$) to carbon c ($C_c$) bond is a double bond; $R_8$ is absent; $R_1$, $R_3$, $R_4$, and $R_7$ are each independently selected from H and halogen; $R_2$ is selected from hydrogen, halogen, —OH, —OR$_9$, —SH, —SR$_9$, —NH2, —NHR$_9$, —NR$_9$R$_{10}$, and $C_1$ to $C_6$ alkyl, wherein $R_9$ and $R_{10}$ are each independently selected from $C_1$ to $C_4$ alkyl; and $R_5$ and $R_6$ are together are

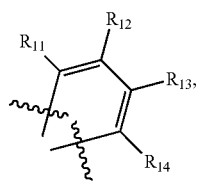

wherein $R_{11}$, $R_{12}$, $R_{13}$, and $R_{14}$ are each independently selected from hydrogen and halogen. In some such embodiments, $R_2$ is selected from hydrogen, halogen, —OH, —OR$_9$, —SH, —SR$_9$, —NH2, —NHR$_9$, —NR$_9$R$_{10}$, and $C_1$ to $C_4$ alkyl, wherein $R_9$ and $R_{10}$ are each independently selected from $C_1$ to $C_3$ alkyl. In some such embodiments, $R_2$ is selected from hydrogen and halogen.

In some embodiments, a compound of Formula I is provided, wherein $X_1$ is NH; $X_2$ is O; $X_3$ is selected from =O, =S, and =NH; the carbon a ($C_a$) to carbon b ($C_b$) bond is a double bond; $R_8$ is selected from hydrogen, halogen, —OH, —SH, and —NH$_2$; $R_1$, $R_3$, $R_4$, and $R_7$ are each independently selected from H and halogen; $R_2$ is selected from hydrogen, halogen, —OH, —OR$_9$, —SH, —SR$_9$, —NH2, —NHR$_9$, —NR$_9$R$_{10}$, and $C_1$ to $C_6$ alkyl, wherein $R_9$ and $R_{10}$ are each independently selected from $C_1$ to $C_4$ alkyl; and $R_5$ and $R_6$ are together are

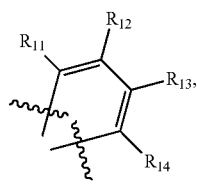

wherein $R_{11}$, $R_{12}$, $R_{13}$, and $R_{14}$ are each independently selected from hydrogen and halogen. In some such embodiments, $R_2$ is selected from hydrogen, halogen, —OH, —OR$_9$, —SH, —SR$_9$, —NH2, —NHR$_9$, —NR$_9$R$_{10}$, and $C_1$ to $C_4$ alkyl, wherein $R_9$ and $R_{10}$ are each independently selected from $C_1$ to $C_3$ alkyl. In some such embodiments, $R_2$ is selected from hydrogen and halogen.

In some embodiments, a compound of Formula I is provided, wherein $X_1$ is O; $X_2$ is N; $X_3$ is selected from =O, =S, and =NH; the carbon a ($C_a$) to carbon b ($C_b$) bond is a double bond; $R_8$ is absent; $R_1$, $R_3$, $R_4$, $R_5$, $R_6$, and $R_7$ are each independently selected from H and halogen; and $R_2$ is selected from hydrogen, halogen, —OH, —OR$_9$, —SH, —SR$_9$, —NH2, —NHR$_9$, —NR$_9$R$_{10}$, and $C_1$ to $C_6$ alkyl, wherein $R_9$ and $R_{10}$ are each independently selected from $C_1$ to $C_4$ alkyl. In some such embodiments, $R_2$ is selected from hydrogen, halogen, —OH, —OR$_9$, —SH, —SR$_9$, —NH2, —NHR$_9$, —NR$_9$R$_{10}$, and $C_1$ to $C_4$ alkyl, wherein $R_9$ and $R_{10}$ are each independently selected from $C_1$ to $C_3$ alkyl. In some such embodiments, $R_2$ is selected from hydrogen, halogen, —OH, —SH, and —NH$_2$.

In some embodiments, a compound of Formula I is selected from the compounds in Table 1, and pharmaceutically acceptable salts thereof

TABLE 1

Nonlimiting exemplary compounds of Formula I

| Compound | Structure |
|---|---|
| 9 | 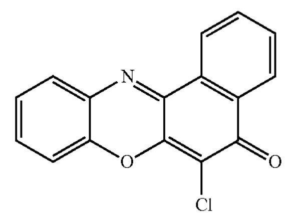 [SMILES: O=c1c(Cl)c2oc3ccccc3nc-2c2ccccc12] |
| 9A | 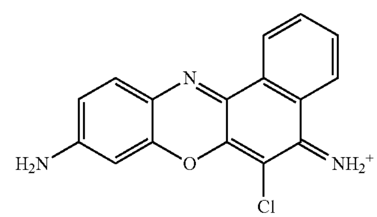 [SMILES: Nc1ccc2nc3c4ccccc4c(=[NH2+])c(Cl)c-3oc2c1] |
| 9B | 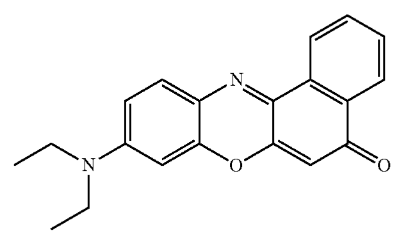 [SMILES: CCN(CC)c1ccc2nc3c4ccccc4c(=O)cc-3oc2c1] |
| 9C | 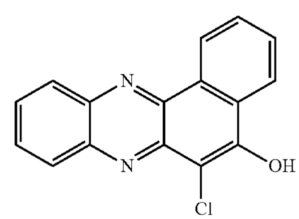 [SMILES: Oc1c(Cl)c2nc3ccccc3nc2c2ccccc12] |
| 9D | 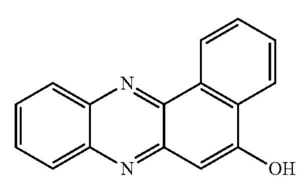 [SMILES: Oc1cc2nc3ccccc3nc2c2ccccc12] |
| 9E | 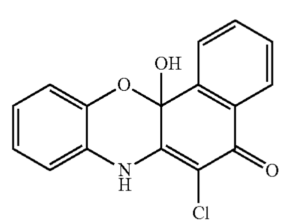 [SMILES: O=C1C(Cl)=C2Nc3ccccc3OC2(O)c2ccccc21] |

TABLE 1-continued

Nonlimiting exemplary compounds of Formula I

| Compound | Structure |
|---|---|
| 9I | 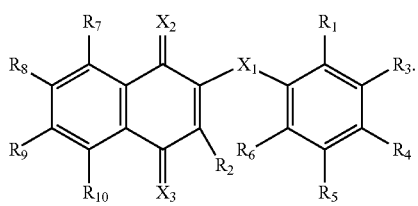 |

In some embodiments, compounds of Formula II and pharmaceutically acceptable salts thereof are provided:

$$\text{II}$$

[Structure of Formula II showing a naphthoquinone-like core with substituents $R_7$, $R_8$, $R_9$, $R_{10}$ on one ring, $X_2$, $X_3$ on the carbonyls, $R_2$, $X_1$ bridging, and a phenyl ring with $R_1$, $R_3$, $R_4$, $R_5$, $R_6$]

In some embodiments, $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_{10}$ alkyl. In some embodiments, $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_8$ alkyl. w In some embodiments, $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_6$ alkyl. In some embodiments, $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_4$ alkyl. In some embodiments, $R_{11}$ and $R_{12}$ are independently selected from $C_1$-$C_6$ alkyl. In some embodiments, $R_{11}$ and $R_{12}$ are independently selected from $C_1$-$C_5$ alkyl. In some embodiments, $R_{11}$ and $R_{12}$ are independently selected from $C_1$-$C_4$ alkyl. In some embodiments, $R_{11}$ and $R_{12}$ are independently selected from $C_1$-$C_3$ alkyl. In some embodiments, $R_{11}$ and $R_{12}$ are independently selected from $C_1$-$C_2$ alkyl. It is to be understood that each $R_{11}$ and $R_{12}$ is independently selected for each substituent that comprises an $R_{11}$ and/or $R_{12}$.

In some embodiments, $R_2$ is selected from hydrogen, halogen, —OH, —SH, and —$NH_2$. In some embodiments, $R_2$ is selected from hydrogen and halogen.

In some embodiments, $R_3$ to $R_{10}$ are each independently selected from hydrogen, halogen, —OH, —$OR_{11}$, —SH, —$SR_{11}$, —$NH_2$, —$NHR_{11}$, —$NR_{11}R_{12}$, and $C_1$-$C_{10}$ alkyl. In some embodiments, $R_3$ to $R_{10}$ are each independently selected from hydrogen, halogen, —OH, —$OR_{11}$, —SH, —$SR_{11}$, —$NH_2$, —$NHR_{11}$, —$NR_{11}R_{12}$, and $C_1$-$C_8$ alkyl. In some embodiments, $R_3$ to $R_{10}$ are each independently selected from hydrogen, halogen, —OH, —$OR_{11}$, —SH, —$SR_{11}$, —$NH_2$, —$NHR_{11}$, —$NR_{11}R_{12}$, and $C_1$-$C_6$ alkyl. In some embodiments, $R_3$ to $R_{10}$ are each independently selected from hydrogen, halogen, —OH, —$OR_{11}$, —SH, —$SR_{11}$, —$NH_2$, —$NHR_{11}$, —$NR_{11}R_{12}$, and $C_1$-$C_4$ alkyl. In some embodiments, $R_{11}$ and $R_{12}$ are independently selected from $C_1$-$C_6$ alkyl. In some embodiments, $R_{11}$ and $R_{12}$ are independently selected from $C_1$-$C_5$ alkyl. In some embodiments, $R_{11}$ and $R_{12}$ are independently selected from $C_1$-$C_4$ alkyl. In some embodiments, $R_{11}$ and $R_{12}$ are independently selected from $C_1$-$C_3$ alkyl. It is to be understood that each $R_{11}$ and $R_{12}$ is independently selected for each substituent that comprises an $R_{11}$ and/or $R_{12}$.

In some embodiments, $R_3$ to $R_{10}$ are each independently selected from hydrogen and halogen.

In some embodiments, $X_1$ is selected from O, S, and NH. In some embodiments, $X_1$ is NH. In some embodiments, $X_2$ and $X_3$ are each independently selected from O, S, and NH. In some embodiments, $X_2$ and $X_3$ are each O.

In some embodiments, a compound of Formula II is provided, wherein $X_1$ is selected from O, S, and NH; $X_2$ and $X_3$ are each independently selected from =O, =S, and =NH; $R_2$ to $R_{10}$ are each independently selected from hydrogen and halogen; and $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_4$ alkyl, wherein $R_{11}$ and $R_{12}$ are independently selected from $C_1$-$C_3$ alkyl. In some such embodiments, $R_1$ is selected from hydrogen, halogen, —OH, —$OR_{11}$, —SH, —$SR_{11}$, —$NH_2$, —$NHR_{11}$, and $C_1$-$C_3$ alkyl, wherein $R_{11}$ is selected from $C_1$-$C_2$ alkyl. In some such embodiments, $R_1$ is selected from hydrogen, halogen, —OH, —$OR_{11}$, —SH, and —$SR_{11}$, wherein $R_{11}$ is selected from $C_1$-$C_2$ alkyl.

In some embodiments, a compound of Formula II is provided, wherein $X_1$ is NH; $X_2$ and $X_3$ are each independently selected from =O and =S; $R_2$ to $R_{10}$ are each independently selected from hydrogen and halogen; and $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_4$ alkyl, wherein $R_{11}$ and $R_{12}$ are independently selected from $C_1$-$C_3$ alkyl. In some such embodiments, $R_1$ is selected from hydrogen, halogen, —OH, —$OR_{11}$, —SH, —$SR_{11}$, —$NH_2$, —$NHR_{11}$, and $C_1$-$C_3$ alkyl, wherein $R_{11}$ is selected from $C_1$-$C_2$ alkyl. In some such embodiments, $R_1$ is selected from hydrogen, halogen, —OH, —$OR_{11}$, —SH, and —$SR_{11}$, wherein $R_{11}$ is selected from $C_1$-$C_2$ alkyl.

In some embodiments, a compound of Formula II is provided, wherein $X_1$ is NH; $X_2$ and $X_3$ are each =O; $R_2$ to $R_{10}$ are each independently selected from hydrogen and halogen; and $R_1$ is selected from hydrogen, halogen, —OH, —$OR_{11}$, —SH, —$SR_{11}$, —$NH_2$, —$NHR_{11}$, —$NR_{11}R_{12}$, and $C_1$-$C_4$ alkyl, wherein $R_{11}$ and $R_{12}$ are independently selected from $C_1$-$C_3$ alkyl. In some such embodiments, $R_1$ is selected from hydrogen, halogen, —OH, —$OR_{11}$, —SH, —$SR_{11}$, —$NH_2$, —$NHR_{11}$, and $C_1$-$C_3$ alkyl, wherein $R_{11}$ is selected from $C_1$-$C_2$ alkyl. In some such embodiments, $R_1$ is selected from hydrogen, halogen, —OH, —$OR_{11}$, —SH, and —$SR_{11}$, wherein $R_{11}$ is selected from $C_1$-$C_2$ alkyl.

In some embodiments, a compound of Formula II is selected from the compounds in Table 2, and pharmaceutically acceptable salts thereof

TABLE 2

Nonlimiting exemplary compounds of Formula II

| Compound | Structure |
|---|---|
| 19 | [Structure showing a 1,4-naphthoquinone substituted with NH-phenyl group bearing ortho-ethoxy, and Cl substituent] |

TABLE 2-continued

Nonlimiting exemplary compounds of Formula II

| Compound | Structure |
|---|---|
| 19A | (structure) |
| 19B | (structure) |

The term "alkyl," as used herein, refers to straight- or branched-chain hydrocarbon radical, which may be fully saturated, or mono- or poly-unsaturated, having the number of carbon atoms designated (i.e., $C_1$-$C_{10}$ means one to ten carbons). Examples of saturated hydrocarbon radicals include, but are not limited to, methyl, ethyl, n-propyl, iso-propyl, n-butyl, t-butyl, isobutyl, homologs and isomers of, for example, n-pentyl, n-hexyl, n-heptyl, n-octyl, etc. An unsaturated alkyl group is one having one or more double bonds or triple bonds. Examples of unsaturated alkyl groups include, but are not limited to, vinyl, 2-propenyl, crotyl, 2-iso-pentenyl, 2-(butadienyl), 2,4-pentadienyl, ethynyl, 1- and 3-propynyl, 3-butynyl, etc. The term "alkyl," unless otherwise noted, includes derivatives of alkyl, including heteroalkyl, substituted alkyl, and substituted heteroalkyl. Alkyl groups that are limited to hydrocarbon groups may be referred to as "homoalkyl".

A "substituted" alkyl or heteroalkyl, as used herein, refers to a straight- or branched-chain alkyl or heteroalkyl that comprises at least one substituent comprising a non-carbon atom selected from halogen, O, N, S, and Se. Nonlimiting exemplary substituents include halogen, —OH, =O, —$CO_2$, —$CO_2R$, —$NH_2$, =NH, —NHR, —NR'R", =N—R, —SH, —SR, —CN, —NO, —$NO_2$, etc., wherein R, R', and R" are independently selected from $C_1$-$C_3$ homoalkyl.

A "heteroalkyl," as used herein, refers to an straight- or branched-chain alkyl in which one or more carbon atoms other than the carbon atom that is attached to the molecule of Formula I or Formula II is replaced with an atom selected from O, N, S, or Se (along with a suitable change in the number of attached atoms according to the valency of the atom replacing carbon). Thus, a $C_4$ heteroalkyl comprises one or more heteroatoms and three or fewer carbon atoms. Nonlimiting exemplary $C_4$ heteroalkyls therefore include, but are not limited to, —$CH_2$—NH—$CH_2$—$CH_3$, —CHF—$CH_2$—O—$CF_3$, —CH($CH_3$)—S—$CH_3$, etc. Certain groups may be characterized in multiple ways. As a nonlimiting example, —$CH_2$—NH—$CH_2$—OH may be described as a $C_4$ heteroalkyl or a $C_3$ substituted heteroalkyl. In such instances, the description that results in the group being included in a genus controls, unless indicated otherwise.

The term "halogen," as used herein, refers to an atom selected from F, Cl, Br, and I.

Provided herein are pharmaceutical compositions. Such compositions include a therapeutically effective amount of a compound of Formula I and/or a compound of Formula II, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, for example, in humans. Further, a "pharmaceutically acceptable carrier" will generally be a non-toxic solid, semisolid or liquid filler, diluent, adjuvant, excipient, vehicle, encapsulating material, or formulation auxiliary of any type. The particular carrier or carriers included in a pharmaceutical composition are typically dependent on the chosen route of administration.

Such pharmaceutically acceptable carriers can be sterile liquids, such as water and oils, including those of petroleum, animal, vegetable or synthetic origin, including peanut oil, soybean oil, mineral oil, sesame oil and the like. Water is a preferred carrier when the pharmaceutical composition is administered intravenously. Saline solutions and aqueous solutions comprising dextrose, glycerol, sorbitol, sodium carboxymethyl cellulose, and the like, can also be employed as liquid carriers, particularly for injectable solutions. In some embodiments, the active ingredient and one or more carriers are in dry form and can be reconstituted with a suitable vehicle, such as water, before use.

Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain wetting or emulsifying agents, or pH buffering agents such as acetates, citrates, phosphates, Hank's solution, Ringer's solution, and lactated Ringer's solution; antibacterial agents such as benzyl alcohol or methyl parabens; antioxidants such as ascorbic acid or sodium bisulfate; chelating agents such as ethylenediaminetetraacetic acid; and agents for the adjustment of tonicity such as sodium chloride or dextrose. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. For transmucosal and transcutaneous administration, penetrants appropriate to the barrier to be permeated are used in the formulation. Such penetrants are generally known in the art. The composition can be formulated as a suppository, with traditional binders and carriers such as triglycerides. Compositions can also be formulated for inhalation. Examples of suitable pharmaceutical carriers and formulations are described, e.g., in "Remington's Pharmaceutical Sciences" by E. W. Martin.

A nonlimiting exemplary pharmaceutical carrier for hydrophobic embodiments of the compounds of the present invention is a co-solvent system comprising benzyl alcohol, a nonpolar surfactant, a water-miscible organic polymer, and an aqueous phase. A nonlimiting exemplary co-solvent system is the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. The proportions of a co-solvent system can be varied considerably without destroying its solubility and toxicity characteristics. Furthermore, the identity of the co-solvent components can be varied; for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, liposomes and emulsions are well known examples of delivery vehicles or carriers for hydrophobic drugs. Certain organic solvents such as dimethylsulfoxide also can be employed, although usually at the cost of greater toxicity. Additionally, compounds of the present invention can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release a drug for a few weeks up to over 100 days.

Pharmaceutical compositions described herein generally contain a therapeutically effective amount of one or more compounds, preferably in purified form, together with a suitable amount of carrier so as to provide the form for proper administration to the patient. The formulation should suit the mode of administration. In some embodiments, a parental preparation can be enclosed in ampoules, disposable syringes or multiple dose vials made of glass or plastic.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Compounds

The following compounds were synthesized as described:
Compound 9.

A mixture of 2,3-dichloro-1,4-naphthoquin (11.35 g, 50 mmol) and o-aminophenol (5.45 g, 50 mmol), and anhydrous potassium acetate (9.8 g, 100 mmol) in absolute ethanol (400 ml) was refluxed for 2 hours. The solvent was removed to 50 ml, and added cold water, filtered. The solid was crystallization in acetone several times obtaining a yellow solid as compound 9 that was matched with the literature report (Agarwal and Schafer, *J. Org. Chem.* 45: 2155-2161 (1980); Agarwal and Schafer, *J. Org. Chem.* 45: 5144-5149 (1980)).

Compound 9.E.

A mixture of 2,3-dichloro-1,4-naphthoquin (2.27 g, 10 mmol) and o-aminophenol (2.18 g, 20 mmol) in 50 ml of ethanol was heated at 60° C. for 0.5 h. The mixture was reduced to 20 ml and diluted with 500 ml of water, and the product was isolated by filtration and dried. The solid was crystallized several times obtaining a yellow solid as compound 9.E that matched with the literature report (Agarwal and Schafer, *J. Org. Chem.* 45: 2155-2161 (1980)).

Compound 9.F.

A mixture of 2,3-dichloro-1,4-naphthoquin (2.27 g, 10 mmol) and o-aminophenol (2.18 g, 20 mmol), and 2 ml concentrated HCl in 50 ml of ethanol was refluxed for 2 h. The mixture was reduced to 20 ml and diluted with 500 ml of water, and the product was isolated by filtration and dried. The solid was crystallized several times obtaining a yellow solid as compound 9.F that matched with the literature report (Agarwal and Schafer, *J. Org. Chem.* 45: 2155-2161 (1980)).

Compound 9.G.

A mixture of 2,3-dichloro-1,4-naphthoquin (2.27 g, 10 mmol) and o-aminophenol (2.18 g, 20 mmol), and 1 ml concentrated HCl in 20 ml of methanol was refluxed on a steam bath for 2 h. The mixture was diluted with 500 ml of water, and the product was isolated by filtration and dried. The solid was crystallized several times obtaining a yellow solid as compound 9.G that matched with the literature report (Agarwal and Schafer, *J. Org. Chem.* 45: 2155-2161 (1980)).

The following compounds were obtained from commercial vendors: 9.A, Sigma-Aldrich, St Louis, Mo., USA (cat. no. 255246); 9.B, Sigma-Aldrich (cat. no. 19123); 9.C, Ryan Scientific, Mt. Pleasant, S.C., USA (cat. no. RDR 00966); 9.D, ChemBridge, San Diego, Calif., USA (cat. no. 5195211); 9.H, Princeton Biomolecular, Princeton, N.J., USA (cat. no. OSSL131788); 9.1, Sigma-Aldrich (cat. no. 424455); 9.J, Ryan Scientific (cat. no. AE-848/01277001); 9.K, Milestone Pharmatech, New Brunswick, N.J., USA (cat. no. 1526735); 9.L, Princeton Biomolecular (cat. no. OSSK__460611); 9.M, Sigma-Aldrich (cat. no. Q1603); 19.A, Ryan Scientific (cat. no. STOCK3S-12829); 19.B, Sigma-Aldrich (cat. no. R750794); 19.C, Princeton Biomolecular (cat. no. OSSL__038866).

Antibodies and Western Blot Analysis

Western blotting was performed on a 4-12% Bis-Tris SDS-PAGE system (NuPAGE; Invitrogen, Carlsbad, Calif., USA) as described previously (Costantini et al., 2006; Jonas et al., 2008; Jonas et al., 2010; Ko and Puglielli, 2007; Ko and Puglielli, 2009; Pehar et al., 2010). The following antibodies were used in this study: anti-acetylated lysine (monoclonal; cat. no. ab409; Abcam, Cambridge, Mass., USA); anti-BACE1 (polyclonal; cat. no. ab2077; Abcam); anti-Myc (monoclonal; cat. no. sc-40; santa cruz, Santa Cruz, Calif., USA); anti-ATases/NAT8 (polyclonal; cat. no. AP4957c; Abgent, San Diego, Calif., USA); anti-actin (monoclonal; cat. no. A1978; Sigma, St Louis, Mo., USA); anti-C99 (monoclonal; cat. no. M066-3; MBL, Woburn, Mass., USA); anti-acetylated H3 (polyclonal; cat. no. 06-599, Millipore, Billerica, Mass.); anti-acetylated H4 (polyclonal; cat. no. 06-866, Millipore, Billerica, Mass.); anti-αPCNA (polyclonal; cat. no. AP2835b, Abgent, San Diego, Calif., USA).

Samples were imaged with classical chemiluminescence and with the LiCor Odyssey Infrared Imaging System (LI-COR Biosciences, Lincoln, Nebr., USA). For chemiluminescent detection, HRP-conjugated anti-mouse or anti-rabbit secondary antibodies were used at 1:6000 dilution in 3% BSA/TBST (GE Healthcare). Detection was performed with either Lumiglo (KPL) or ECL Plus (GE Healthcare). For infrared imaging, goat anti-rabbit Alexa Fluor 680-conjugated secondary antibodies were used. For quantification, values were normalized to the appropriate loading control (shown in the figures).

Real Time PCR

Total RNA was isolated using RNeasy Plus Mini Kit (Qiagen, Valencia, Calif., USA). One μg of total RNA was randomly reverse transcribed using SuperScript III reverse transcriptase (Invitrogen, Carlsbad, Calif., USA) according to the manufacturer's instructions. Quantitative PCRs were carried out in a LightCycler480 Real-time PCR System (Roche, Indianapolis, Ind., USA) using LightCycler480 SYBR Green I Master Mix (Roche). The cycling parameters were as follows: 95° C., 10 seconds; 55° C., 10 seconds; 72° C., 15 seconds, for a maximum of 40 cycles.

Controls without reverse transcription were included in each assay. PCR primers specific to each gene were as follows:

```
ATase1/NAT8B-human,
forward
                                    (SEQ ID NO: 1)
5'-CGATTACTGAAGCTGCCTCGA-3', reverse
                                    (SEQ ID NO: 2)
5'-GGTTTTTTGGCAAGGAACCAC-3';

ATase2/NAT8-human,
forward
                                    (SEQ ID NO: 3)
5'-TCCTTGCCAAAAAACCCTGG-3', reverse
                                    (SEQ ID NO: 4)
5'-ATGCCCACCACCTTCTCTTCA-3'.
```

ATase1 and ATase2 expression levels were normalized against GAPDH levels and are expressed as percent of control. PCR primers specific to GAPDH were as follows:

```
Glyceraldehyde-3-phosphate dehydrogenase
(GAPDH)-human,
forward
                                    (SEQ ID NO: 5)
5'-GAAGGTGAAGGTCGGAGTC-3', reverse
                                    (SEQ ID NO: 6)
5'-GAAGATGGTGATGGGATTTC-3';
```

AcetylCoA:lysine acetyltransferase Assay

The acetyl:CoA lysine acetyltransferase activity of ATase1 and ATase2 was assayed as described before (Ko and Puglielli, 2009). Briefly, we adapted a commercially available fluorescent kit (cat. no. 10006515, Cayman Chemicals) as follows: as source of the enzymatic activity, we used affinity purified ATase1-myc and ATase2-myc at the final concentration of 300 ng/μl; as donor of the acetyl group, we used acetyl-CoA at the final concentration of 12.5 μM. ATase1 and ATase2 were purified with the ProFound c-Myc-Tag IP/Co-IP Kit (Pierce) as suggested by the manufacturer and already described in our previous work (Ko and Puglielli, 2009). The acetyltransferase assay was performed as recommended by the manufacturer.

For kinetic analysis of ATase1 and ATase2 inhibition, the assays were performed in the presence of the indicated concentrations of compound 9, 19 and 9.I. The concentration of acetyl-CoA was varied from 0.5 to 15 mM. Values were plotted as a Lineweaver-Burk plot using Graphpad Prism software.

Aβ Determination

For Aβ determinations in the conditioned media, H4 cells were plated in 6-well Petri dishes. When 80-90% confluent, cells were washed in PBS and incubated in 1 ml of fresh medium for 48 hr. Secreted Aβ was determined by standard sandwich ELISA as described before (Costantini et al., 2007; Costantini et al., 2006; Jonas et al., 2008; Jonas et al., 2010; Ko and Puglielli, 2009; Pehar et al., 2010). For each sample, the levels of Aβ40, Aβ42, and Aβtotal were quantified as triplicate based upon standard curves run (on every ELISA plate) and then expressed as pmol Aβ/mg of protein. Aβ42 was constantly found to be ~25% of total Aβ values.

Preparation of Cytosolic and Nuclear Fractions

Cytosolic and nuclear extracts were prepared as described before (Ko and Puglielli, 2007). For cytosolic extracts, cells were homogenized in homogenization buffer containing 25 mM Tris-HCl, pH 7.4, 0.5 mM EDTA, 0.5 mM EGTA, and a protease inhibitor mixture. The homogenates were centrifuged at 14,000×g for 15 min, and supernatants were collected as cytosolic proteins.

For nuclear extracts cells were scraped into ice-cold phosphate-buffered saline and collected by centrifugation. The cell pellets were suspended in 3 volumes of lysis buffer (20 mM Hepes, pH 7.9, 10 mM KCl, 1 mM EDTA, pH 8.0, 0.2% Nonidet P-40, 10% glycerol, and a protease inhibitor mixture) followed by incubation on ice for 10 min. Cell suspensions were gently pipetted up and down; the lysates were then centrifuged at 14,000×g for 5 min at 4° C. to obtain nuclear pellets. Nuclear pellets were washed twice with cell lysis buffer (lacking Nonidet P-40 and protease inhibitor mixture) and then resuspended in 2 volumes of nuclear extract buffer (20 mM Hepes, pH 7.9, 10 mM KCl, 1 mM EDTA, pH 8.0, 420 mM NaCl, 20% glycerol, and a protease inhibitor mixture). The nuclei were extracted by incubation at 4° C. for 30 min with gentle agitation followed by centrifugation at 14,000×g at 4° C. for 5 min; the resultant supernatant fraction was used as a nuclear extract.

Statistical Analysis

Results are always expressed as mean±S.D. of the indicated number of determinations. The data were analyzed by ANOVA and Student's t test comparison, using GraphPad InStat3 software. Statistical significance was reached at $P>0.05$.

Example 2

ATase1 and ATase2 are Expressed in Neurons and are Up-Regulated in Alzheimer's Disease Brains To confirm the relevance of ATase1 and ATase2 for AD neuropathology, we first assessed whether they are expressed in the brain and in cellular systems that are relevant for the study of the nervous system. FIG. 1A shows that the commercially available antibody used in this study could recognize transgenic ATase1 and ATase2 in Chinese Hamster Ovary (CHO) cells over-expressing myc-tagged versions of the human proteins. Neither acetyltransferase could be significantly detected in non-transfected CHO cells. We next assessed the expression levels of the endogenous acetyltransferases in human neuroglioma (H4), human neuroblastoma (SH-SY5Y and SHEP) and rat pheochromocytoma (PC-12) cells as well as mouse primary neurons and mouse cerebral cortex. Both ATase1 and ATase2 were identified, albeit with different intensity (FIG. 1B). Specifically, ATase1 appeared to be equally expressed while ATase2 appeared to be more predominant in H4, SH-SY5Y and SHEP cells. Detection of ATase2 in PC-12 cells required longer exposure (FIG. 1B; right panel). Assessment of a total extract of mouse cerebral cortex showed significant expression of ATase1 but very low expression of ATase2 (FIG. 1B; lane 8). However, both were easily detectable in mouse primary neurons suggesting a preferential expression of the ATases in neurons (FIG. 1B).

Figure 5:
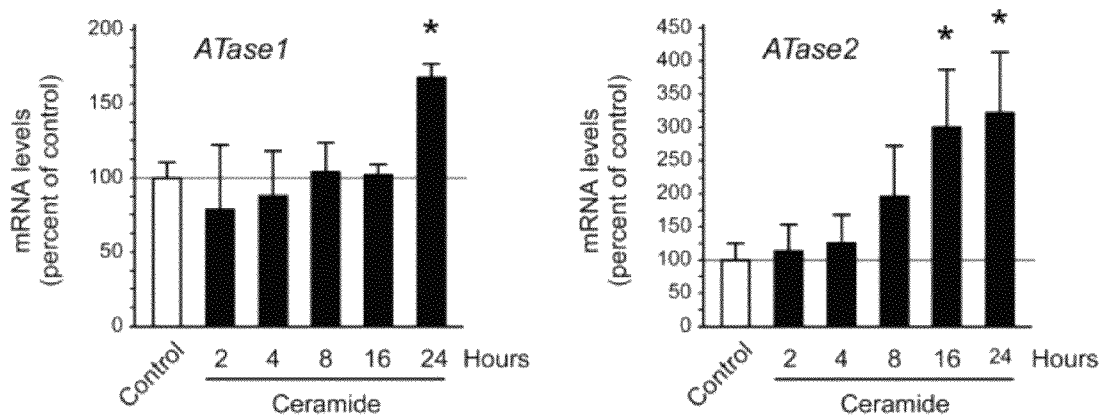
FIG. 5. ATase2 is more tightly regulated by lipid second messenger ceramide. H4 cells were treated with 10 μM ceramide for the indicated time prior to quantitative real-time PCR. Results are the average (n=4)±S.D. *, P<0.05.

Interestingly, the expression levels of ATase2 increased with the age of the primary neurons (FIG. 1B; compare lane 6 and 7). Both we and other groups have shown that, when in culture, primary neurons display an internal timing that mimics cellular senescence (Costantini, 2006;Shen, 2006). In particular, we reported that the levels of endogenous ceramide increase with the age of the culture (Costantini, 2006). We also reported that ceramide treatment increases the mRNA levels of both ATase1 and ATase2 (Ko and Puglielli, 2009). Therefore, the activation of ATase2 in "older" neurons is consistent with our previous findings. We also noticed that ATase2 is more tightly regulated by ceramide than ATase1 (FIG. 5). Therefore, the above results indicate that both acetyltransferases are expressed in the brain and neurons as well as in cell lines that are commonly used for the study of the nervous system. They also suggest that in contrast to ATase1, which is constitutively expressed, ATase2 acts as a regulated form of acetylCoA:lysine acetyltransferase.

Direct assessment of ATase1 and ATase2 mRNA levels in the brain of late-onset AD patients revealed a significant increase, when compared to age-matched controls (FIG. 1C). Although these results might indicate disease-relevant functions, they do not prove a direct cause-effect type of relationship between ATase1/ATase2 levels and AD neuropathology. In fact, results obtained with postmortem AD tissue might be influenced by the long duration of the disease, which could affect the genetic profile of the tissue. However, they are consistent with previous work showing that AD patients also have a 3-fold increase in the levels of ceramide in brain areas that are affected by AD neuropathology ((Han, 2002;Cutler, 2004); reviewed in (Puglielli, 2008)). We have already reported that the levels of both ATases are tightly regulated by the lipid second messenger ceramide (FIG. 5; see also (Ko and Puglielli, 2009)).

Example 3

ATase1 and ATase2 Inhibitors Down-Regulate Both Levels and Activity of BACE1

Figure 6:
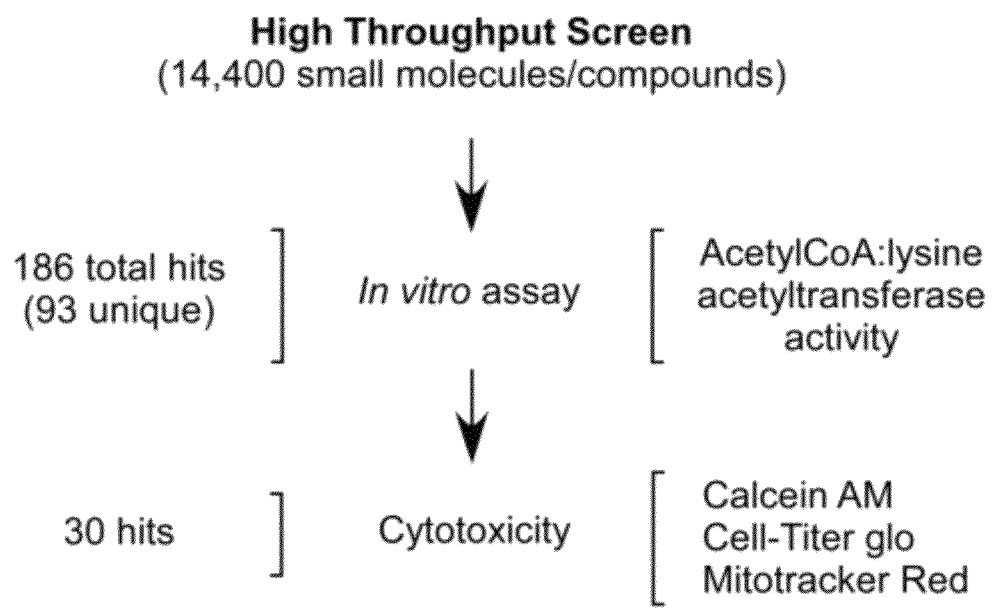
FIG. 6. Summary of the strategy used to identify the compounds tested in this study. Of the 186 compounds identified with the in vitro assay, 93 were unique to our screen (never identified as positive hits in other screens). The cytotoxicity assay included Calcein AM incorporation, Cell-Titer glo and Mitotracker Red.

We previously described a fluorescent assay that is able to assess the acetylCoA:lysine acetyltransferase activity of ATase1 and ATase2 in vitro (Ko and Puglielli, 2009). The assay employs affinity purified ATase1 or ATase2 (as enzymes), acetyl-CoA (as donor of the acetyl group) and a recombinant peptide corresponding to the N-terminal tail of the histone protein H3 (as acceptor of the acetyl group). The H3 peptide was preferred to affinity purified BACE1 because it is acetylated in a conformation independent manner ((Ko and Puglielli, 2009) and data not shown) and, therefore, more suitable for large screening approaches. To identify possible ATase1 and ATase2 inhibitors we used the assay to screen a single library of 14,400 small molecules/compounds. The screen identified 186 small molecules/compounds able to inhibit ATase1, ATase2 or both in vitro. Importantly, 93 compounds were unique to our screen suggesting unique properties. Each compound was then screened for cytotoxic properties by using multi-plex cytotoxicity assays on a variety of cell lines, including human neuroblastoma and human neuroglioma. Of the above 186 small molecules/compounds, only 30 did not cause significant cytotoxicity when used at 10 µM final concentration. A summary of the screen is shown in FIG. 6. The above 30 compounds were individually screened on human neuroglioma (H4) cells for their ability to reduce the levels of BACE1 and the generation of Aβ. Two compounds, 9 and 19, produced significant changes and were object of further study.

Figure 2:
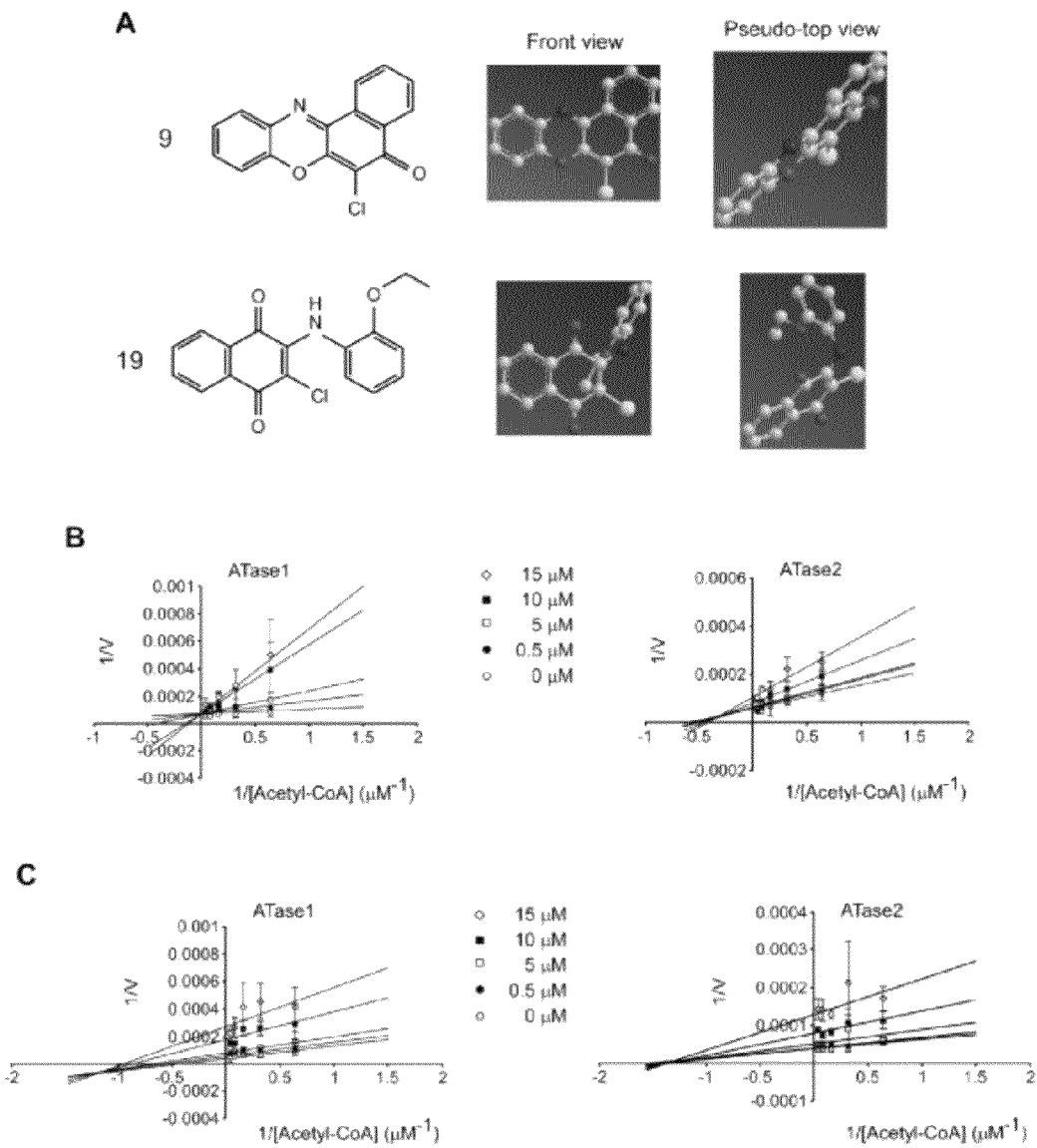
FIG. 2. Inhibition kinetics of compound 9 and 19. (A) Schematic representation of the chemical and structural features of compound 9 and 19. (B and C) Lineweaver-Burke plots for compound 9 (B) and 19 (C). Results are the average of at least 6 independent determinations ±S.D.
Figure 3:
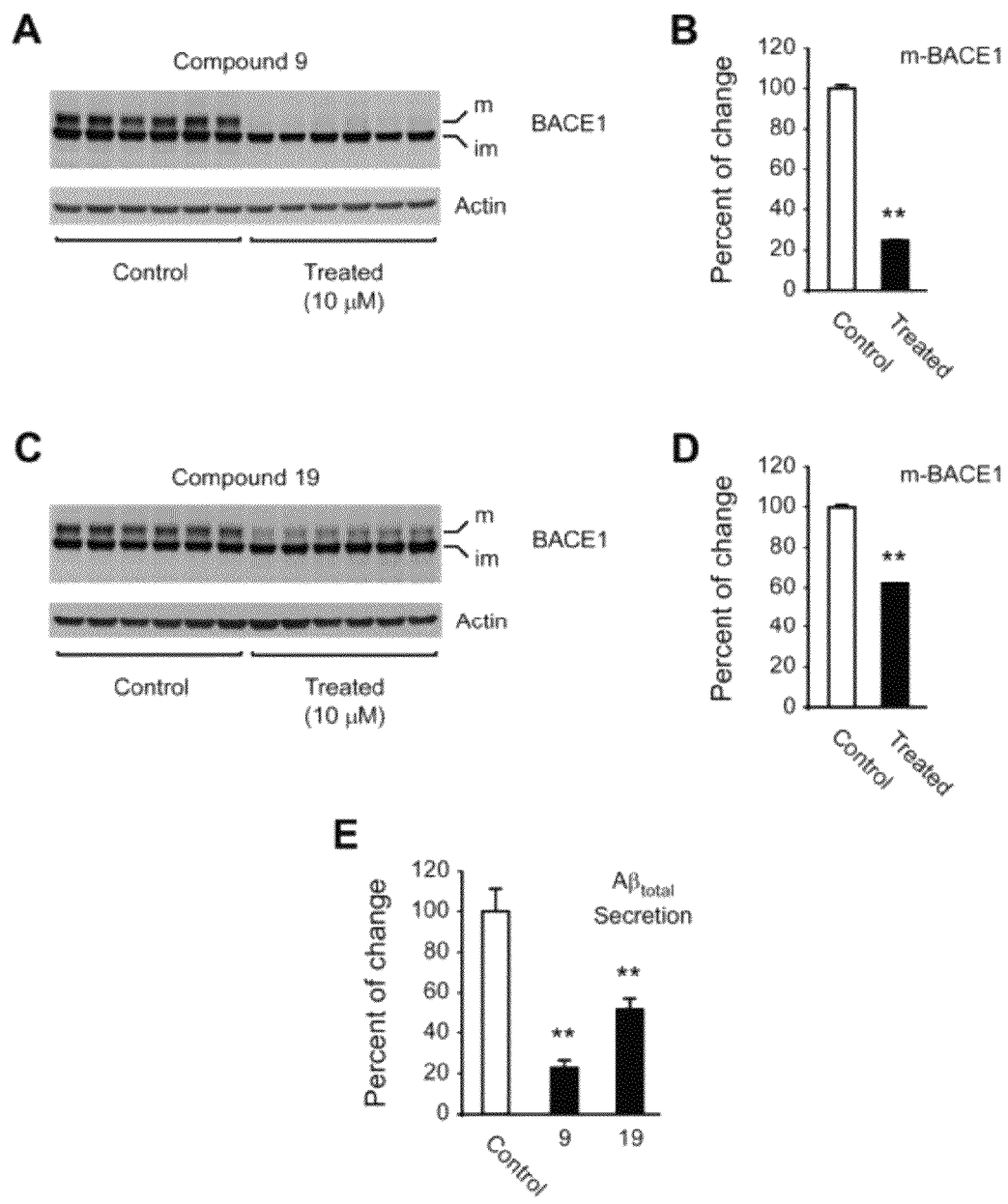
FIG. 3. Compound 9 and 19 decrease the endogenous levels of BACE1. (A-F) H4 cells were treated with either compound 9 or 19 for 48 hours prior to Western blot assessment of BACE1 levels in total cell lysates (A-D) and ELISA determination of secreted Aβ (E). Representative Western blots are shown in (A) and (C) while respective quantifications are shown in (B) and (D). Results in (B), (D) and (E) are the average (n=6)±S.D. **, P<0.005.

The compounds display very different chemical and structural features (FIG. 2A), which probably explain the different kinetics of inhibition for acetyl-CoA, the donor of the acetyl group. In fact, compound 9 displayed a competitive inhibition with ATase1 and a non-competitive inhibition with ATase2 while compound 19 displayed non-competitive inhibition with both enzymes (FIGS. 2B,C). The IC50 for compound 9 was ~3.9 µM for ATase1 and ~0.79 µM for ATase2; the IC50 for compound 19 was ~13.3 µM for ATase1 and 18.2 µM for ATase2. The fact that compound 9 uses two different mechanisms of reversible inhibition with ATase1 and ATase2 is consistent with our early report showing that, although highly identical, the two enzymes display a few biochemical differences (Ko and Puglielli, 2009).

To assess their biological effects, we treated human neuroglioma (H4) cells with 10 µM of both compounds. In both cases, we observed a significant reduction in the levels of BACE1 (FIGS. 3A-D), although compound 9 appeared to act as a more potent inhibitor. This might reflect different kinetics of inhibition as well as different IC50s (see FIG. 2). Alternatively, it might also be explained by different cell-permeability properties. In fact, the cLog P for compound 9 and 19 is 5.03 and 3.19, respectively. The cLog P (or partition coefficient) is an indication of partition properties of a compound between hydrophobic and hydrophilic compartments. Higher values indicate preferential distribution in hydrophobic environments and, as such, increased permeability across biological membranes.

Figure 7:
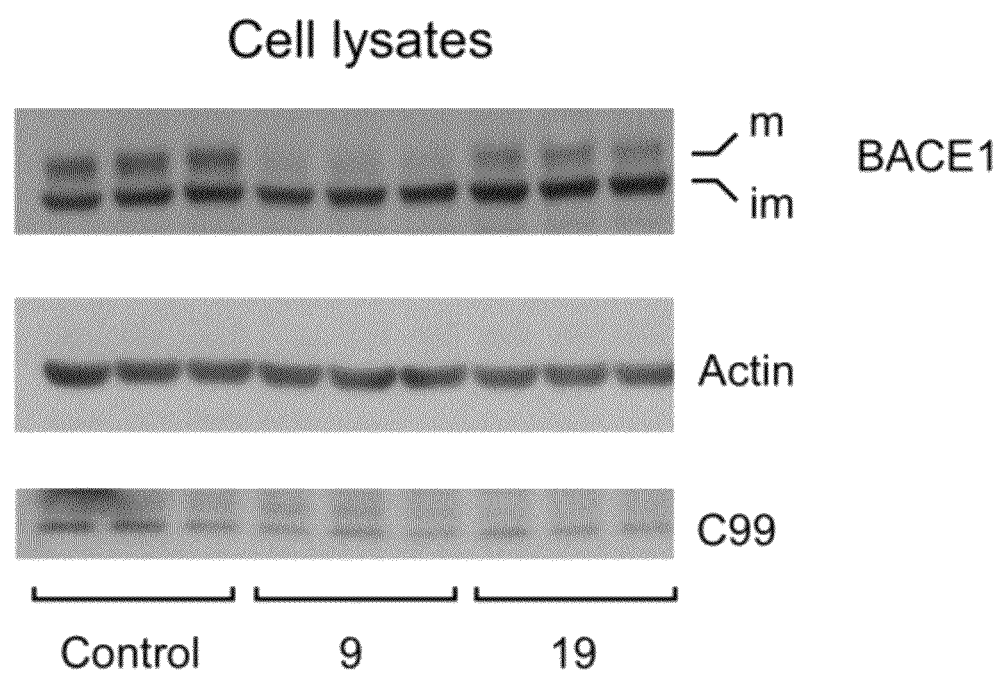
FIG. 7. Compound 9 and 19 decrease levels and activity of BACE1. H4 cells were treated with either compound 9 or 19 for 48 hours prior to Western blot assessment of BACE1 and C99 levels in cell lysates. C99 is the immediate product of BACE1-mediated cleavage of APP.

Interestingly, both compounds preferentially affected the mature form of BACE1 (FIGS. 3A,C). We previously reported that the ER-based acetylation of nascent BACE1 prevalently affects the levels of mature BACE1 (Costantini, 2007;Ko and Puglielli, 2009). In fact, non-acetylated mutants of BACE1 are correctly synthesized in the ER but rapidly degraded in the ERGIC before they can complete maturation (Costantini, 2007;Jonas, 2008). The decreased levels of BACE1 were paralleled by decreased levels of Aβ in the conditioned media (FIG. 3E) and decreased cellular levels of C99 (FIG. 7). As mentioned above, C99 is the immediate product of BACE1-mediated cleavage of APP, whereas Aβ represents one of the final products of the sequential processing of APP by BACE1 and γ-secretase (Puglielli, 2008). Parallel changes in C99 and Aβ directly reflect the steady-state levels and activity of BACE1. Taken together, the above results indicate that both compound 9 and 19 affect the metabolism of BACE1 and the rate of Aβ generation.

Figure 8:
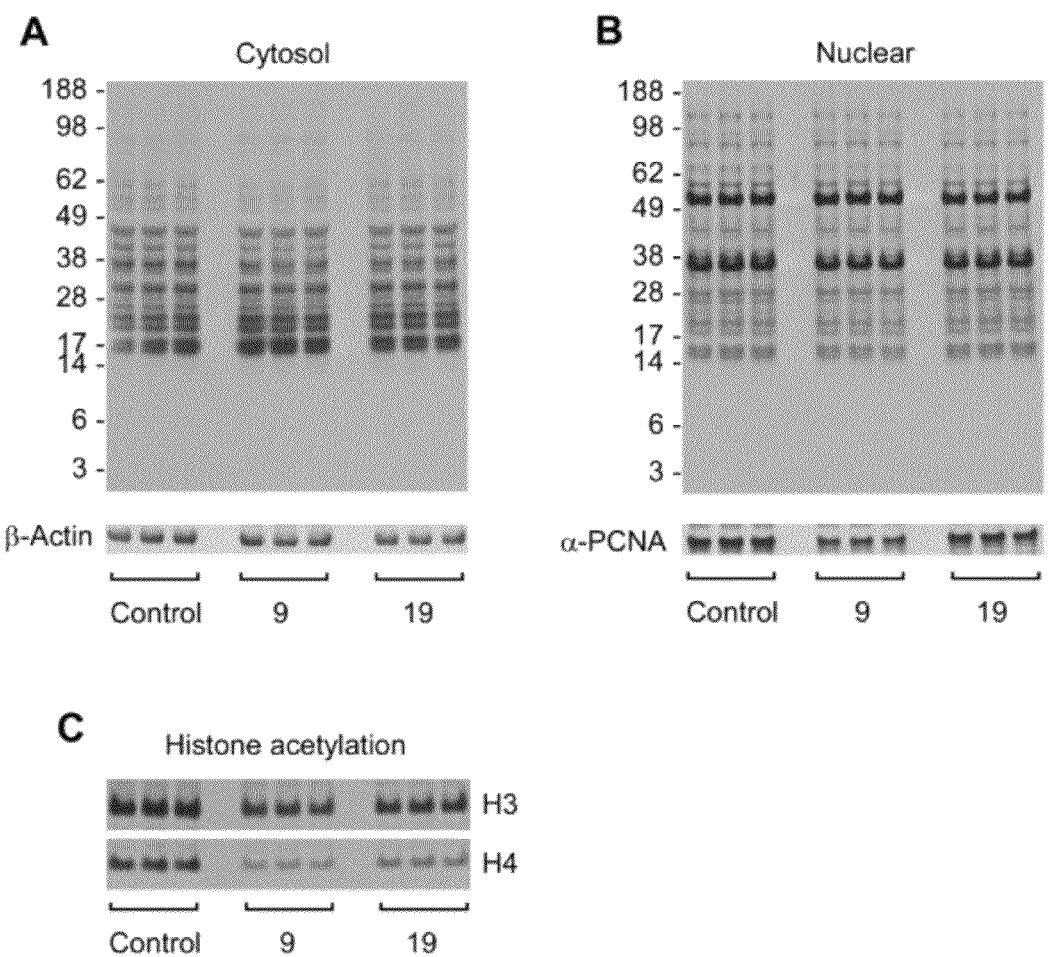
FIG. 8. Compound 9 and 19 do not affect the lysine acetylation profile of cytosolic or nuclear proteins. (A and B) H4 cells were treated with either compound 9 or 19 for 48 hours prior to Western blot assessment of the acetylation profile of cytosolic (A) and nuclear (B) proteins. (C) The nuclear fraction used in (B) was also used to assess the lysine acetylation profile of the histone proteins H3 and H4.

Lysine acetylation was initially discovered as a covalent modification of nuclear and cytosolic proteins, which included histones, different families of transcription factors and cytoskeleton-associated proteins (Yang and Seto, 2007). Therefore, it is possible that, although screened for their ability to inhibit ATase1 and ATase2 in vitro, compound 9 and 19 might interfere with the acetylation of several other classes of proteins. To address this point we decided to assess the acetylation profile of both cytosolic and nuclear proteins. Neither compound 9 nor compound 19 produced significant changes (FIGS. 8A,B). However, direct assessment of the acetylation profile of the histone protein H3 and H4 revealed a slight reduction (FIG. 8C). This effect was more evident with histone H4 then H3. When taken together, the results displayed in FIG. 8 suggest that compound 9 and compound 19 are highly selective. In fact, the most evident decrease in lysine acetylation was observed with histone H4 suggesting that they only interfere with the acetyl-CoA:lysine acetyltransferase activity of a very limited number of non-ER acetyltransferases, perhaps specific to histone H4. It is also worth stressing that neither compound inhibited the in vitro activity of the histone acetyltransferase p300/CBP (data not shown).

Next we decided to analyze structure-activity properties of both compounds. In the case of compound 9, we designed 13 different chemical derivatives and assessed IC50s in vitro. The results displayed in Table 3 show that some modifications improved while others abolished the inhibitory properties of the parent compound.

TABLE 3

$IC_{50s}$ of compound 9 derivatives

| Compound | $IC_{50}$ (μM) | | | | | | | |
|---|---|---|---|---|---|---|---|---|
| | 9 | 9.A | 9.B | 9.C | 9.D | 9.E | 9.F | 9.G | 9.H |
| ATase 1 | 3.9 | 2.09 | 1.92 | 1.03 | 17.58 | 12.46 | >100 | >100 | >100 |
| ATase2 | 0.79 | 0.4 | 0.39 | 0.16 | 2.04 | 2.35 | >100 | >100 | >100 |

| | $IC_{50}$ (μM) | | | | |
|---|---|---|---|---|---|
| Compound | 9.I | 9.J | 9.K | 9.L | 9.M |
| ATase 1 | 2.48 | >100 | >100 | >100 | >100 |
| ATase2 | 0.55 | >100 | >100 | >100 | >100 |

Figure 9:
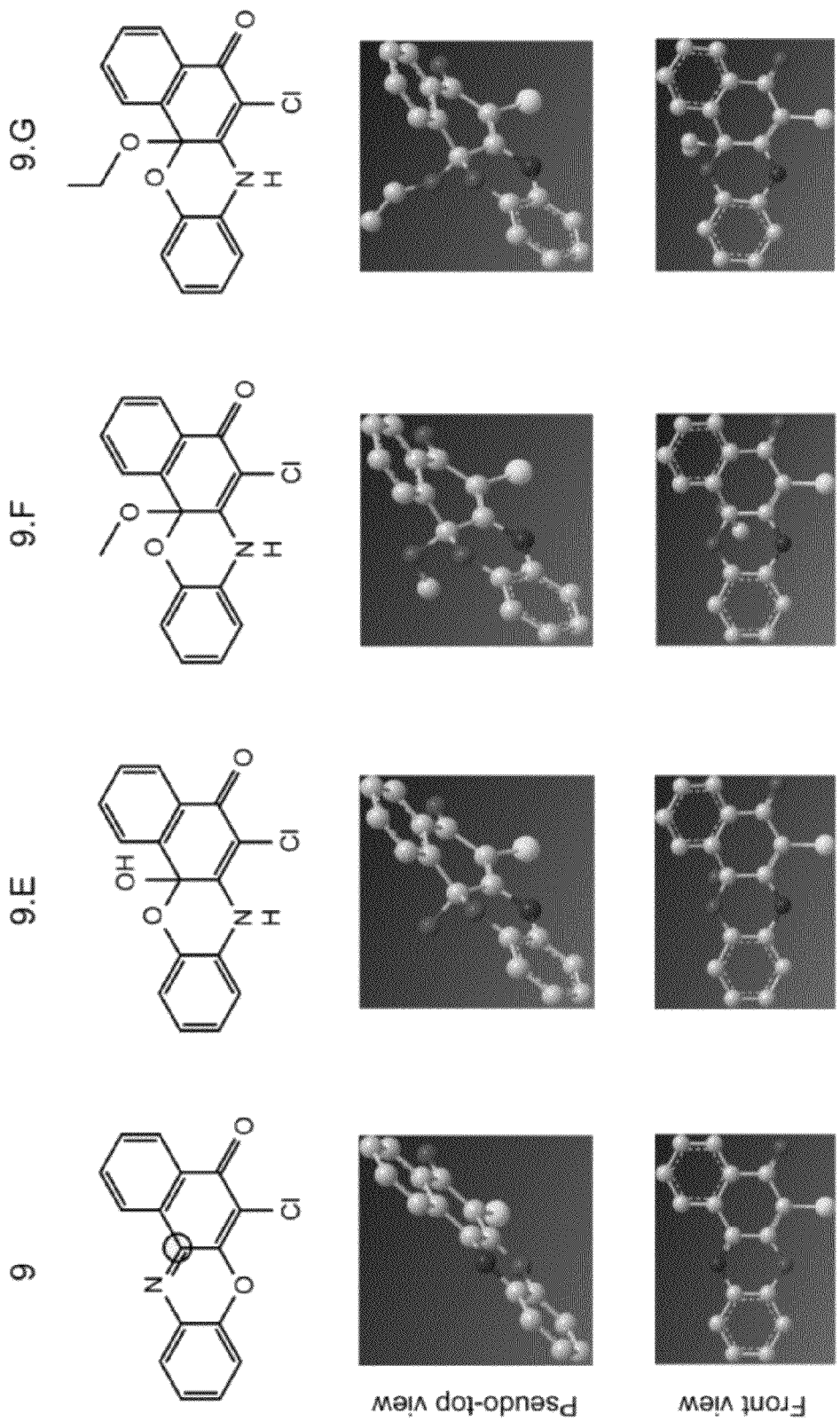
FIG. 9. Schematic representation of the chemical and structural features of compound 9.E, 9.F and 9.G. The site of relevant modification in the parent compound is circled. The structure is shown as pseudo-top and front views.
Figure 10:
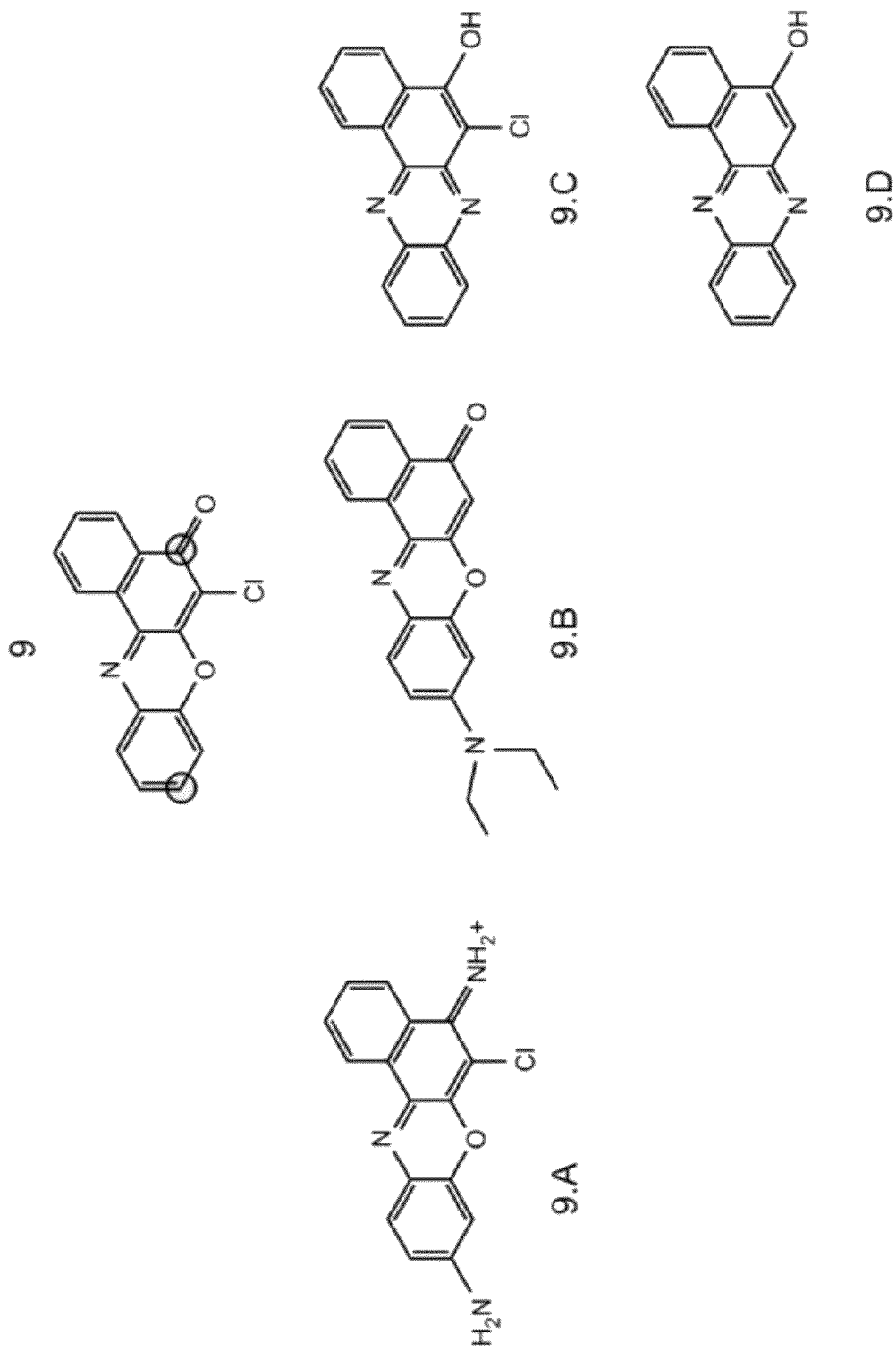
FIG. 10. Schematic representation of the chemical features of compound 9.A, 9.B, 9.0 and 9.D. The sites of relevant modification in the parent compound are circled.
Figure 11:
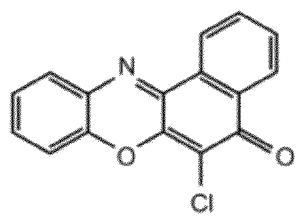
FIG. 11. Schematic representation of the chemical features of compound 9.H-9.M.
Figure 11:
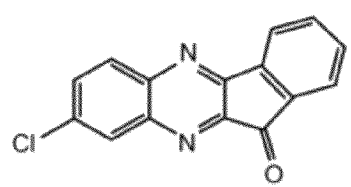
Figure 11:
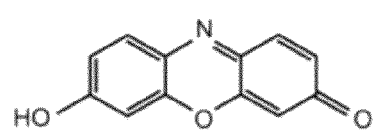
Figure 11:
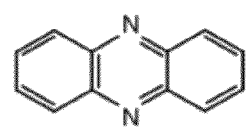
Figure 11:
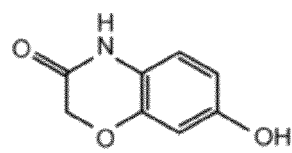
Figure 11:
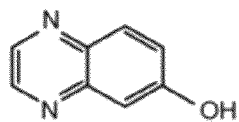
Figure 11:
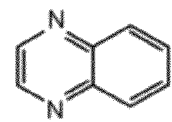

Although the trend was overall similar, we observed some degree of difference when comparing IC50s for ATase1 and ATase2, suggesting that certain structural determinants affect the two enzymes differently (Table 3). The progressive loss of activity observed with derivatives 9.E-9.G is particularly interesting because it highlights an important structural feature (FIG. 9). In fact, compound 9.E is a rearranged acetal in which the central ring junction is pyramidalized by the presence of a hydroxyl group. This compound is bent slightly relative to the planar compound 9 (FIG. 9; pseudo-top view) and shows decreased activity (Table 3). Replacement of this hydroxyl group with methoxyl or ethoxyl group obliterates activity (Table 3); these modifications also appear to cause a more pronounced bending of the molecule based on modeling (FIG. 9; pseudo-top view), and suggest that the planar structure of compound 9 is essential for its inhibitory activity. In contrast, the modifications introduced in derivatives 9.A-9.D revealed areas that can be modified without affecting the enzymatic properties (FIG. 10; marked in yellow). The region highlighted in the "left" ring is particularly interesting because easily accessible and can be functionalized for a variety of purposes, such as increasing solubility, attachment to cell-penetrating peptides, or conjugation to biomolecules. The highest activity was observed for compound 9.0 in which the central ring oxygen was replaced with nitrogen and the carbonyl-containing ring was tautomerized to a phenol, suggesting that these modifications can be beneficial. However, shrinking the carbonyl-containing ring to a 5-membered ring obliterated the activity (compound 9.H of Table 3; see also FIG. 11) indicating that the 6-membered ring is critical. Finally, reduction of the structure of the parent compound to three or two rings resulted in a complete loss of activity (FIG. 11). The only exception was derivative 9.1, which retained inhibitory properties (Table 3; see also FIG. 11). The only significant difference between 9.I and 9.J was in one hydroxyl and one oxygen group, which are missing in 9.J (FIG. 11).

Figure 12:
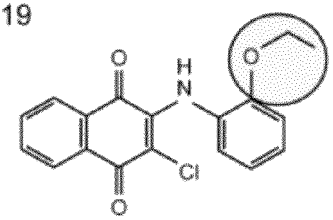
FIG. 12. Schematic representation of the chemical features of compound 19.A, 19.B and 19.C. The site of relevant modification in the parent compound is circled.
Figure 12:
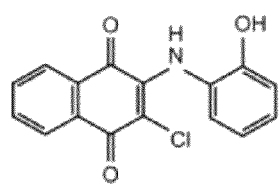
Figure 12:
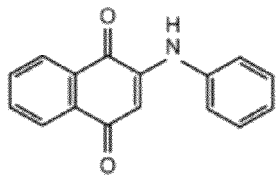
Figure 12:
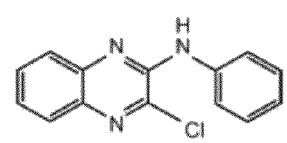

The results obtained with the derivatives of compound 19 were much more dramatic. In fact, removal of the right sidechain (see FIG. 12; highlighted) reduced or completely abolished the activity (Table 4). Reduction of the structure to a two ring unit also abolished activity (data not shown). Therefore, overall the activity of compound 19 is tightly linked to the side chain on the fourth ring and does not offer room for modifications that could be used to improve biological properties.

TABLE 4

$IC_{50s}$ of compound 19 derivatives

| Compound | $IC_{50}$ (μM) | | | |
|---|---|---|---|---|
| | 19 | 19.A | 19.B | 19.C |
| ATase 1 | 13.3 | 12.19 | 42.68 | >100 |
| ATase2 | 18.2 | 47.35 | >100 | >100 |

In conclusion, when taken together, the above results clearly indicate that the inhibitory properties of both compound 9 and 19 are tightly dependent on their structure. This conclusion probably explains the high degree of selectivity that we observed in cellular systems (see FIG. 3 and FIG. 8).

Example 4

Compound 9 Causes Degradation of the ATases

Figure 4:
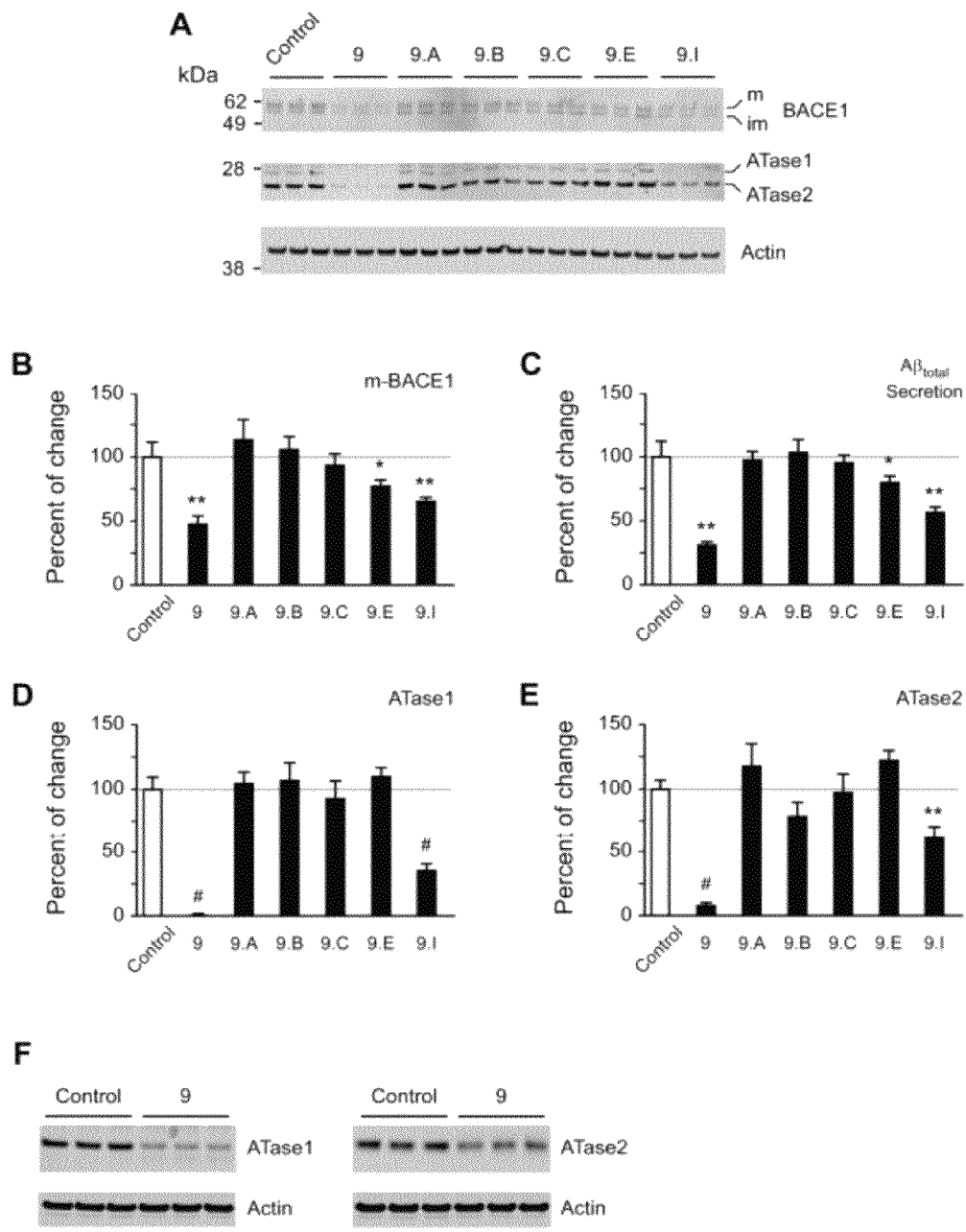
FIG. 4. Compound 9 causes degradation of the ATases. (A) H4 cells were treated with the indicated compounds (10 μM) for 48 hours prior to Western blot assessment of BACE1 and ATase1/ATase2 levels in total cell lysates. (B, D and E) Quantification of changes are expressed as percent of control (no treatment) and are the average (n=3)±S.D. *, P<0.05; **, P<0.005; #, P<0.0005. (C) ELISA determination of secreted Aβ in the conditioned media of the experiment described in (A). Results are expressed as percent of control (no treatment) and are the average (n=3)±S.D. *, P<0.05; **, P<0.005. (F) CHO cells over-expressing either ATase1 or ATase2 were treated with compound 9 (10 μM) for 48 hours prior to Western blot assessment of ATase1 and ATase2 levels in total cell lysates.
Figure 13:
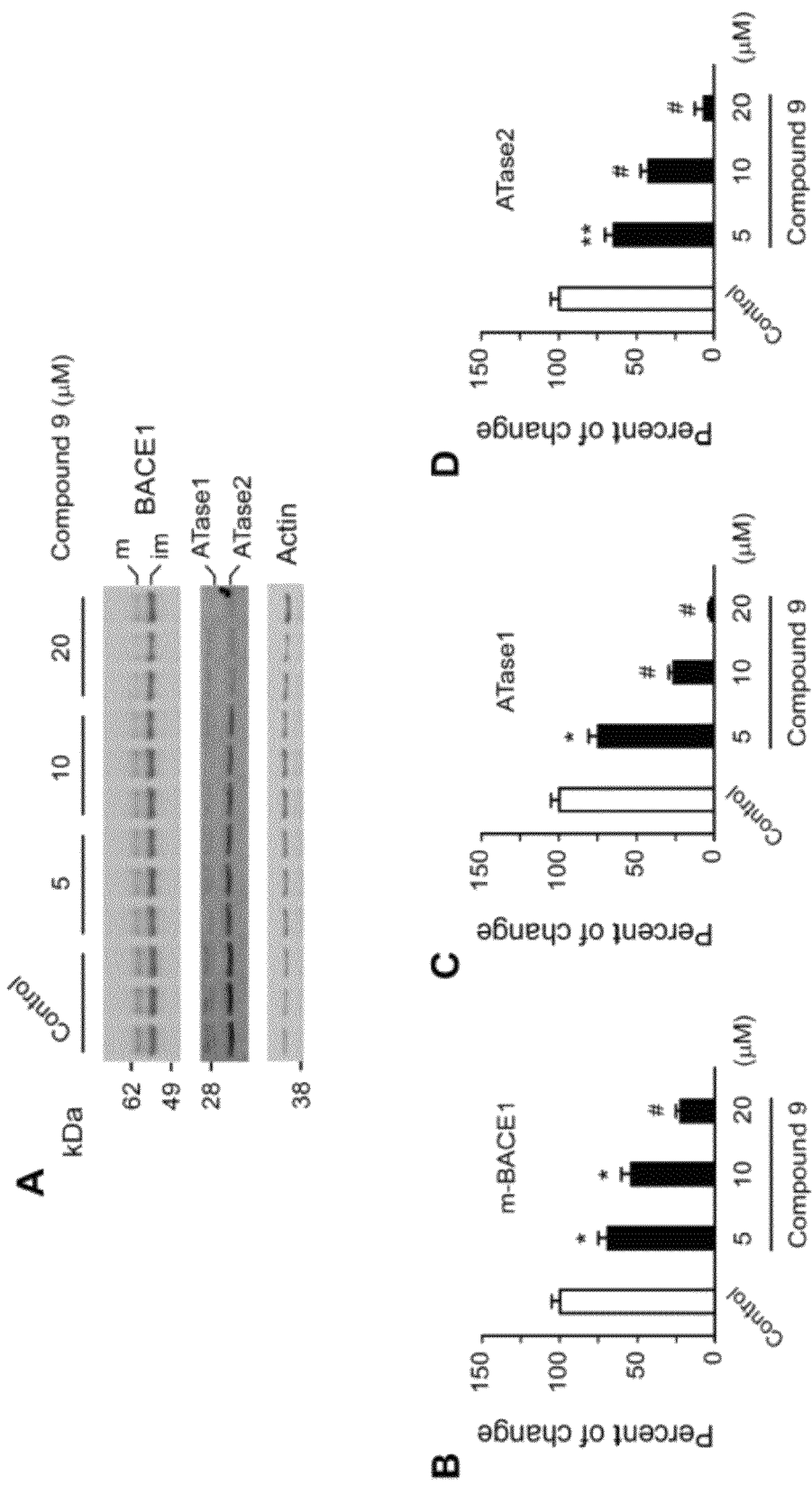
FIG. 13. Compound 9 decreases the levels of both ATase1 and ATase2. (A) H4 cells were treated with the increasing concentrations of compound 9 for 48 hours prior to Western blot assessment of BACE1 and ATase1/ATase2 levels in total cell lysates. (B-D) Quantification of changes are expressed as percent of control (no treatment) and are the average (n=3) ±S.D. *, P<0.05; **, P<0.005; #, P<0.0005.

To assess whether the chemical modifications introduced in compound 9 also affected the biological properties, we tested the most active derivatives in cellular systems. H4 cells were treated with 10 μM of compound 9, 9.A, 9.B, 9.C, 9.E and 9.I. The results show that only 9.I retained significant ability to affect the levels of BACE1 (FIGS. 4A,B) and the generation of Aβ (FIG. 4C). Surprisingly, these results appeared to correlate with the endogenous levels of ATase1 and ATase2 (FIGS. 4A,D,E). In fact, both compound 9 and 9.I were able to significantly down-regulate the acetyltransferases (FIGS. 4A,D,E). Compound 9, which was more active in down-regulating BACE1 levels, also produced a more dramatic decrease in the levels of the ATases (FIGS. 4A,D,E). Finally, compound 9.I appeared to affect ATase1 more dramatically than ATase2 (FIGS. 4A,D,E). The close relationship between levels of the ATases and BACE1 was dose dependent. In fact, increasing concentrations of compound 9 caused a dose-dependent decrease in the levels of both the ATases and BACE1 (FIG. 13). This behavior is consistent with our previous results where we over-expressed or down-regulated the ATases (Ko and Puglielli, 2009). Since, the above experiments might potentially be affected by our ability to detect endogenous ATase1 and ATase2, we also treated CHO cells over-expressing transgenic ATase1 or ATase2. Western blot assessment of ATase1 and ATase2 levels confirmed that compound 9 significantly decreases the levels of both proteins.

Example 5

Compound 9 Crosses the Blood Brain Barrier and Shows Beneficial Effects in AD Mouse Model Compound 9 Crosses the Blood Brain Barrier To assess BBB permeability properties, a group of 5 wild-type mice received 50 mg/kg/day of compound 9 for 1 week. Animals were then sacrificed and CSF collected for biochemical analysis. Treatment was limited to 1 week because this length of time is usually sufficient to reach equilibrium in biological fluids (Ito, et al., 1998; Singh, 2006; Houston and Galetin, 2008). Concentration and duration of the treatment was based on previous studies with drug-like compounds having similar mass and solubility properties (Ito, et al., 1998; Singh, 2006; Houston and Galetin, 2008).

Figure 14:
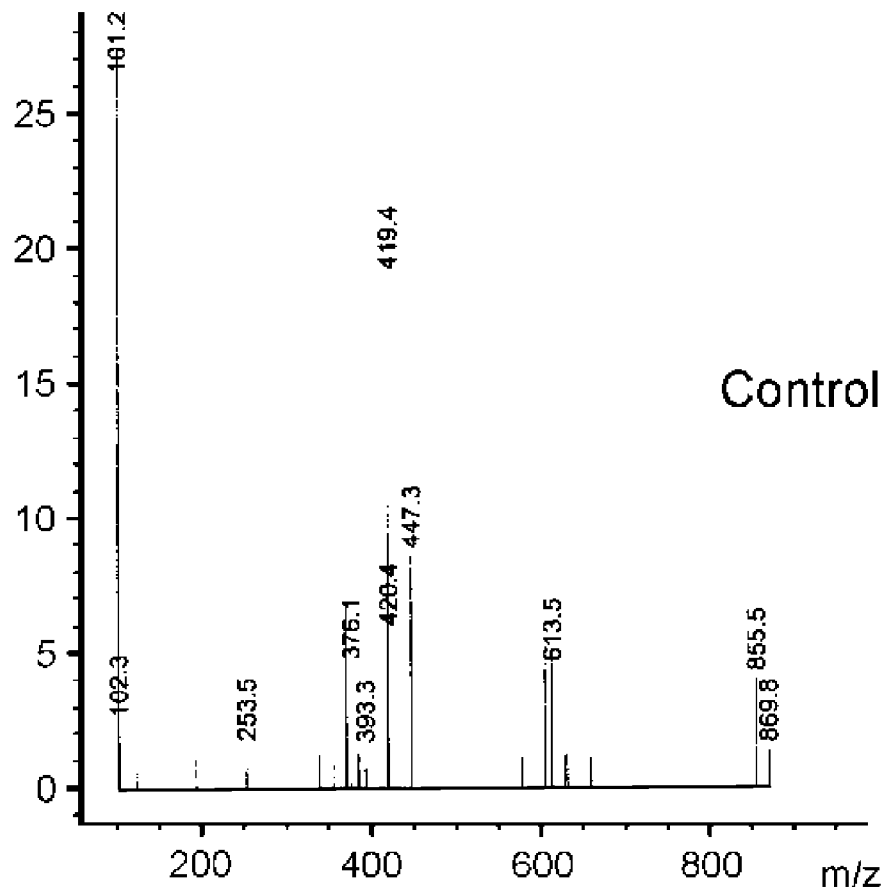
FIG. 14. Compound 9 is able to cross the BBB. Wild-type mice (n=5) were fed a diet containing 50 mg/kg/day of compound 9 for one week and then sacrificed. Control animals (n=5) received placebo-containing pellets. CSF was collected and analyzed by mass spectrometry (MS) to detect compound 9. The pick corresponding to compound 9 is indicated. Results show MS data for 2 treated (FIGS. 14B and 14C) and 1 control (placebo) animal (FIG. 14A). Because of the strong hydrophobic properties of the compound, elution was in 100% methanol. Under these conditions most of compound 9 was found protonated and complexed as follows: 1 molecule of compound 9 (protonated):3 molecules of water (1 protonated):1 molecule of methanol. The total mass of the eluted complex was 369.4. This complex is only generated when adding methanol during the elution process for the MS. Compound 9 was never observed in control animals.
Figure 14:
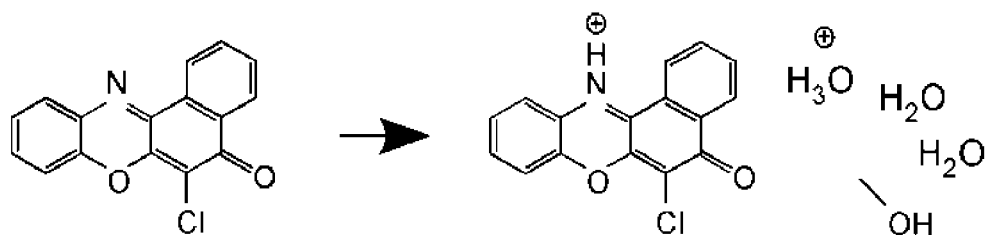
Figure 14:
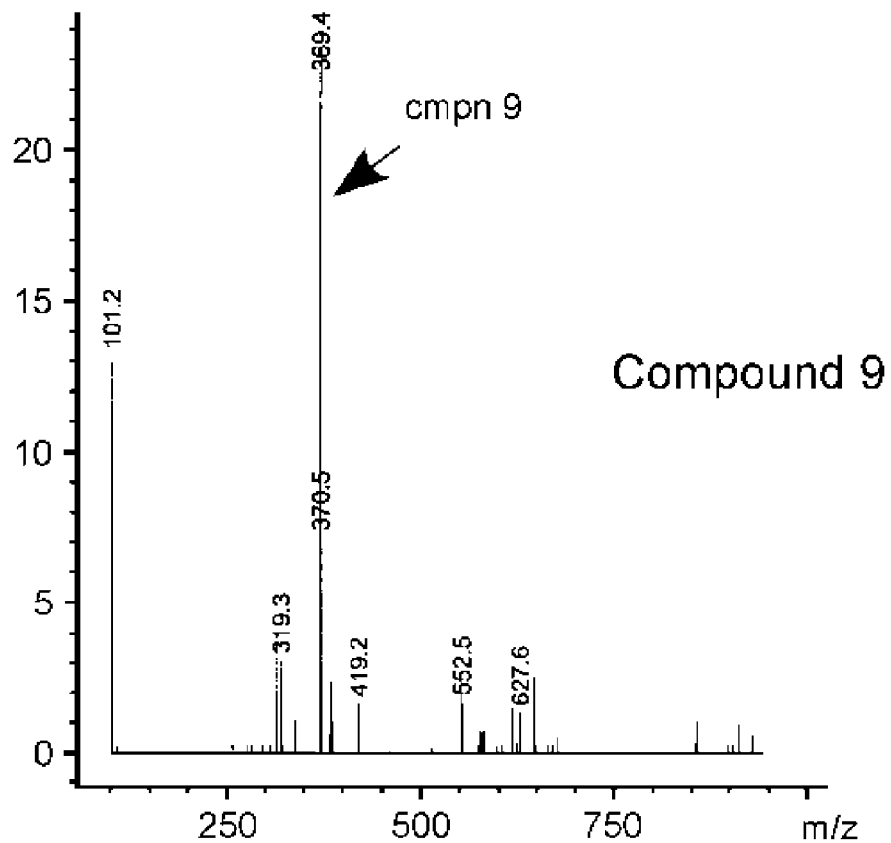
Figure 14:
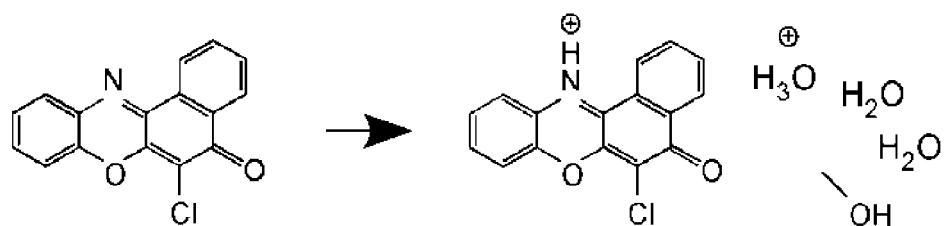
Figure 14:
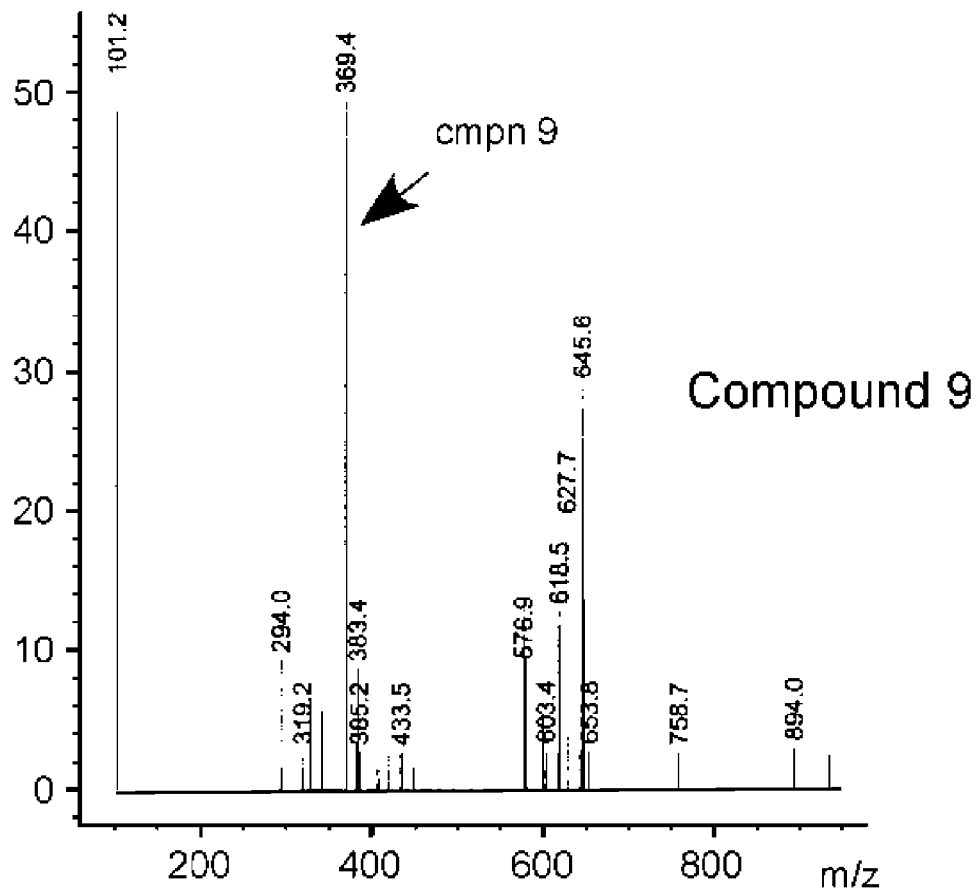
Figure 14:
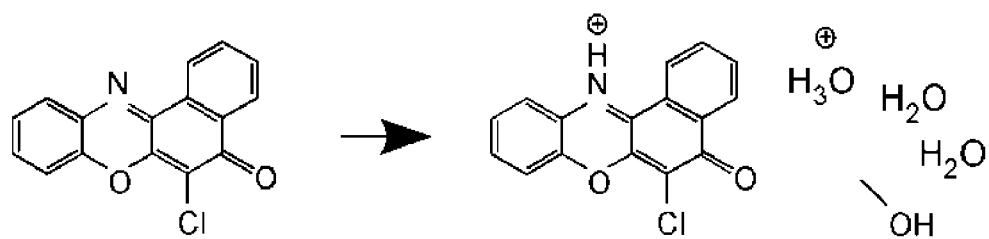

Mass spectrometric assessment of the CSF was able to detect compound 9 in all treated animals, confirming our earlier predictions (FIG. 14).

Compound 9 Prevents LTP Defects and Reduces BACE1 and Aβ Levels in Mouse AD Model In order to assess disease-relevant functions, we performed a pilot study with $APP_{695/swe}$ mice, a commonly-used mouse model of AD. $APP_{695/swe}$ mice express a modified mouse APP cDNA encoding the 695-amino acid isoform with a "humanized" Aβ domain that includes the familial AD-associated Swedish double mutation. $APP_{695/swe}$ mice develop synaptic deficits at 3-5 months of age, well before any sign of neurodegeneration can be observed. The cognitive deficits as well as the amyloid plaques can be detected only later, at approximately 12-18 months of age (reviewed in Duyckaerts, et al., 2008).

A group of non-transgenic and $APP_{695/swe}$ mice were fed a diet containing 50 mg/kg/day of compound 9. Treatment started at weaning (~6 weeks of age) and lasted 4 months. At the end of treatment, the animals were sacrificed and the electrophysiological properties of hippocampal brain slices (as induced by theta burst stimulation to the Schaffer collaterals) were studied.

Figure 15:
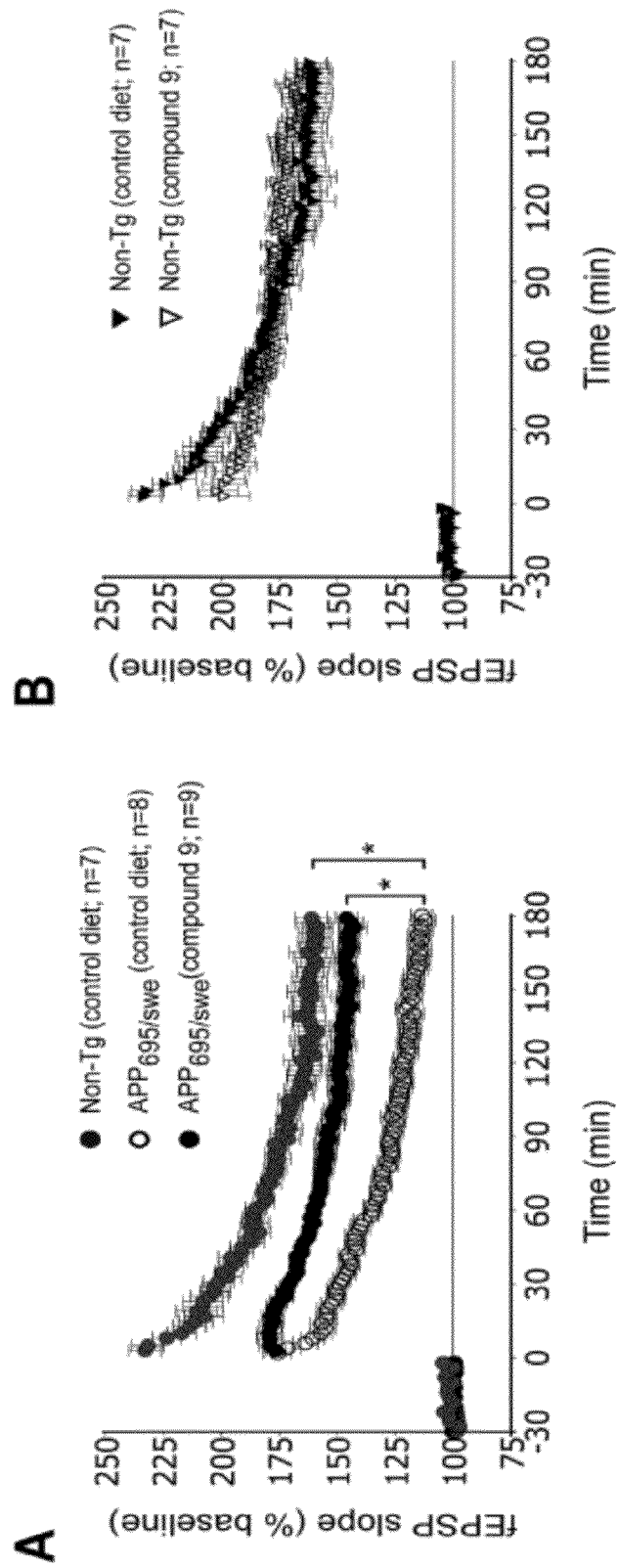
FIG. 15. Compound 9 prevents synaptic deficits in $APP_{695/swe}$ mice. Non-Transgenic (Non-Tg) and $APP_{695/swe}$ mice were fed a diet containing 50 mg/kg/day of compound 9 for 4 months prior to synaptic assessment. Compound 9 prevented the severe deficits of the late component of long term potentiation (LTP) that characterizes the $APP_{695/swe}$ phenotype (A). The compound did not affect the intrinsic properties of synaptic activity in Non-Tg animals (B). Field excitatory postsynaptic potential (fEPSP) as percent of baseline (100) is shown as a function of time. Calibration: 1 mV, 1 ms. All values are mean±SEM. *P<0.0001.

As described in our previous work (Pehar, et al., 2010), $APP_{695/swe}$ mice displayed a marked defect in the late component of the long-term potentiation (LTP) (FIG. 15A) in the absence of significant deficits in the presynaptic component of synaptic transmission (data not shown; see Pehar, et al., 2010). However, these changes were drastically prevented by compound 9. Importantly, no effect was observed in non-transgenic mice (FIG. 15B), indicating that the compound acts by preventing disease-relevant events rather than by improving intrinsic synaptic properties.

Figure 16:
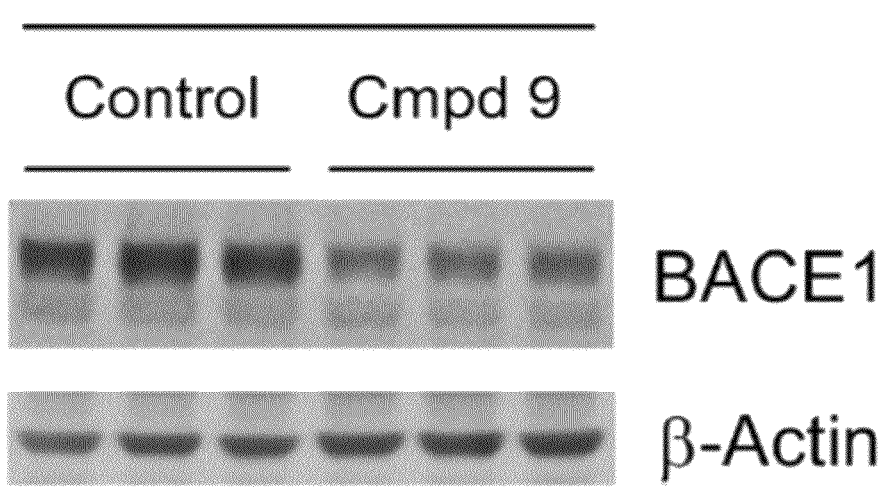
FIG. 16. Compound 9 decreases levels of BACE1 in brain tissue homogenates of $APP_{695/swe}$ transgenic mice. Compound 9 was administered to select transgenic mice for four months, beginning at weaning, with additional transgenic mice used as controls. Brain tissue homogenates were obtained from sacrificed transgenic mice and Western blot assessment of BACE1 in brain tissue homogenates was performed.

The electrophysiological changes were also accompanied by a marked reduction in BACE1 levels (FIG. 16) and a ~50% reduction in soluble Aβ in the brain homogenates of $APP_{695/swe}$ transgenic mice (Table 5). Note that at this age, the animals have not yet developed plaques. As expected from our previous results in cellular models (Ko and Puglielli, 2009), no effect on the $A\beta_{42}/A\beta_{total}$ ratio was observed (data not shown). In fact compound 9 affects BACE1 levels and, as such, impacts on the generation of all Aβ species.

TABLE 5

Aβ levels in brain homogenates (cortex) of $APP_{695/swe}$ mice.

| | Aβ (ng/gr) | |
|---|---|---|
| Control diet | 335 ± 41 | |
| Compound 9 | 178 ± 14 | P < 0.005 |

The foregoing description is considered as illustrative only and is not intended to limit the claimed invention. Numerous modifications and changes may readily occur to those skilled in the art. The invention is not limited to the exact construction and operation shown and described, and accordingly, all suitable modifications and equivalents are considered to fall within the scope of the invention.

REFERENCES

Cai, H., Wang, Y., McCarthy, D., Wen, H., Borchelt, D. R., Price, D. L. and Wong, P. C. (2001). BACE1 is the major beta-secretase for generation of Abeta peptides by neurons. Nat Neurosci 4, 233-4.

Cleary, J. P., Walsh, D. M., Hofmeister, J. J., Shankar, G. M., Kuskowski, M. A., Selkoe, D. J. and Ashe, K. H. (2005). Natural oligomers of the amyloid-beta protein specifically disrupt cognitive function. Nat Neurosci 8, 79-84.

Costantini, C., Ko, M. H., Jonas, M. C. and Puglielli, L. (2007). A reversible form of lysine acetylation in the ER and Golgi lumen controls the molecular stabilization of BACE1. Biochem J 407, 383-95.

Costantini, C., Scrable, H. and Puglielli, L. (2006). An aging pathway controls the TrkA to p75(NTR) receptor switch and amyloid beta-peptide generation. Embo J 25, 1997-2006.

Cutler, R. G., Kelly, J., Storie, K., Pedersen, W. A., Tammara, A., Hatanpaa, K., Troncoso, J. C. and Mattson, M. P. (2004). Involvement of oxidative stress-induced abnormalities in ceramide and cholesterol metabolism in brain aging and Alzheimer's disease. Proc Natl Acad Sci USA 101, 2070-5.

Duyckaerts, C., Potier, M. C., and Delatour, B. (2008). Alzheimer disease models and human neuropathology: similarities and differences. Acta Neuropathol 115:5-38.

Ghosal, K., Vogt, D. L., Liang, M., Shen, Y., Lamb, B. T. and Pimplikar, S. W. (2009). Alzheimer's disease-like pathological features in transgenic mice expressing the APP intracellular domain. Proc Natl Acad Sci USA 106, 18367-72.

Giliberto, L., Zhou, D., Weldon, R., Tamagno, E., De Luca, P., Tabaton, M. and D'Adamio, L. (2008). Evidence that the Amyloid beta Precursor Protein-intracellular domain lowers the stress threshold of neurons and has a "regulated" transcriptional role. Mol Neurodegener 3, 12.

Haass, C. and Steiner, H. (2001). Protofibrils, the unifying toxic molecule of neurodegenerative disorders? Nat Neurosci 4, 859-60.

Han, X., D, M. H., McKeel, D. W., Jr., Kelley, J. and Morris, J. C. (2002). Substantial sulfatide deficiency and ceramide elevation in very early Alzheimer's disease: potential role in disease pathogenesis. J Neurochem 82, 809-18.

Houston, J. B., and Galetin, A. (2008). Methods for predicting in vivo pharmacokinetics using data from in vitro assays. Curr Drug Metab 9:940-951.

Ito, K., Iwatsubo, T., Kanamitsu, S., Nakajima, Y., and Sugiyama, Y. 1998. Quantitative prediction of in vivo drug clearance and drug interactions from in vitro data on metabolism, together with binding and transport. Annu Rev Pharmacol Toxicol 38:461-499.

Jonas, M. C., Costantini, C. and Puglielli, L. (2008). PCSK9 is required for the disposal of non-acetylated intermediates of the nascent membrane protein BACE1. EMBO Rep 9, 916-22.

Jonas, M. C., Pehar, M. and Puglielli, L. (2010). AT-1 is the ER membrane acetyl-CoA transporter and is essential for cell viability. J Cell Sci 123, 3378-88.

Klein, W. L., Krafft, G. A. and Finch, C. E. (2001). Targeting small Abeta oligomers: the solution to an Alzheimer's disease conundrum? Trends Neurosci 24, 219-24.

Ko, M. H. and Puglielli, L. (2007). The sterol carrier protein SCP-x/pro-SCP-2 gene has transcriptional activity and regulates the Alzheimer disease gamma-secretase. J Biol Chem 282, 19742-52.

Ko, M. H. and Puglielli, L. (2009). Two Endoplasmic Reticulum (ER)/ER Golgi Intermediate Compartment-based Lysine Acetyltransferases Post-translationally Regulate BACE1 Levels. J Biol Chem 284, 2482-92.

Lambert, M. P., Barlow, A. K., Chromy, B. A., Edwards, C., Freed, R., Liosatos, M., Morgan, T. E., Rozovsky, I., Trommer, B., Viola, K. L. et al. (1998). Diffusible, nonfibrillar ligands derived from Abeta1-42 are potent central nervous system neurotoxins. Proc Natl Acad Sci USA 95, 6448-53.

Lansbury, P. T., Jr. (1999). Evolution of amyloid: what normal protein folding may tell us about fibrillogenesis and disease. Proc Natl Acad Sci USA 96, 3342-4.

Luo, Y., Bolon, B., Kahn, S., Bennett, B. D., Babu-Khan, S., Denis, P., Fan, W., Kha, H., Zhang, J., Gong, Y. et al. (2001). Mice deficient in BACE1, the Alzheimer's beta-secretase, have normal phenotype and abolished beta-amyloid generation. Nat Neurosci 4, 231-2.

Pehar, M., O'Riordan, K. J., Burns-Cusato, M., Andrzejewski, M. E., del Alcazar, C. G., Burger, C., Scrable, H. and Puglielli, L. (2010). Altered longevity-assurance activity of p53:p44 in the mouse causes memory loss, neurodegeneration and premature death. Aging Cell 9, 174-90.

Puglielli, L. (2008). Aging of the brain, neurotrophin signaling, and Alzheimer's disease: is IGF1-R the common culprit? Neurobiol Aging 29, 795-811.

Puzzo, D., Privitera, L., Leznik, E., Fa, M., Staniszewski, A., Palmeri, A. and Arancio, O. (2008). Picomolar amyloid-beta positively modulates synaptic plasticity and memory in hippocampus. J Neurosci 28, 14537-45.

Shen, Q., Wang, Y., Dimos, J. T., Fasano, C. A., Phoenix, T. N., Lemischka, I. R., Ivanova, N. B., Stifani, S., Morrisey, E. E. and Temple, S. (2006). The timing of cortical neurogenesis is encoded within lineages of individual progenitor cells. Nat Neurosci 9, 743-51.

Singh, S. S. (2006). Preclinical pharmacokinetics: an approach towards safer and efficacious drugs. Curr Drug Metab 7:165-182.

Yang, X. J. and Seto, E. (2007). HATs and HDACs: from structure, function and regulation to novel strategies for therapy and prevention. Oncogene 26, 5310-8.

I claim:

1. A method of treating, delaying the onset of, slowing the progression of, or alleviating at least one symptom of Alzheimer's disease comprising administering to a patient a pharmaceutical composition comprising an effective amount of an inhibitor of ATase1 and/or ATase2, wherein the inhibitor of ATase1 and/or ATase2 is a compound selected from the compounds having the following formula:

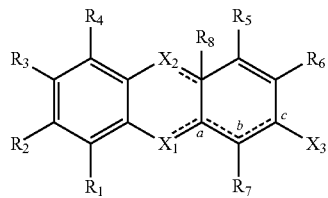

wherein:
$R_1$, $R_2$, $R_3$, $R_4$, and $R_7$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl, wherein $R_9$ and $R_{10}$ are independently selected from $C_1$-$C_5$ alkyl;
$R_8$ is selected from hydrogen, halogen, —OH, —$NH_2$, and —SH, or is absent;
$R_5$ and $R_6$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl, wherein $R_9$ and $R_{10}$ are independently selected from $C_1$-$C_5$ alkyl; or $R_5$ and $R_6$ together are

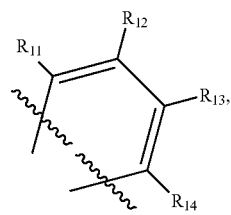

wherein $R_{11}$, $R_{12}$, $R_{13}$, and $R_{14}$ are each independently selected from hydrogen, halogen, —OH, —$OR_9$, —SH, —$SR_9$, —$NH_2$, —$NHR_9$, —$NR_9R_{10}$, and $C_1$-$C_{10}$ alkyl, wherein $R_9$ and $R_{10}$ are independently selected from $C_1$-$C_5$ alkyl;
$X_1$ is selected from N, NH, and O;
$X_2$ is selected from N and O;
$X_3$ is selected from —OH, =O, —$NH_2$, =NH, —SH, and =S; and wherein the $X_1$ to carbon a ($C_a$) bond and the carbon b ($C_b$) to carbon c ($C_c$) bond are both double bonds, or the $C_a$ to $C_b$ bond is a double bond;

or pharmaceutically acceptable salts thereof;

whereby Alzheimer's disease in the patient is delayed in onset, or slowed in progression, or whereby at least one symptom of Alzheimer's disease is alleviated.

2. The method of claim 1, wherein the inhibitor of ATase1 and/or ATase2 is selected from the group consisting of:

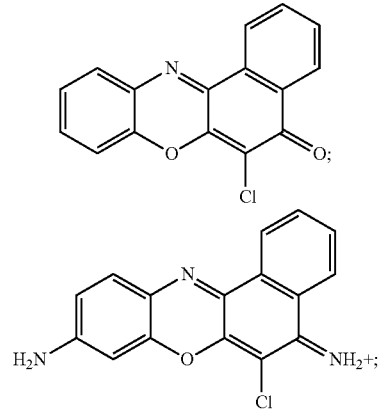

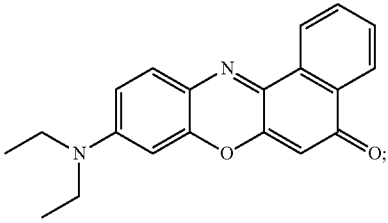

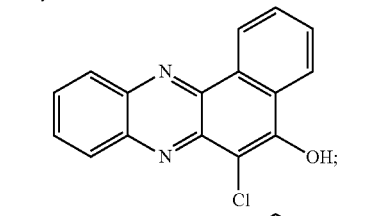

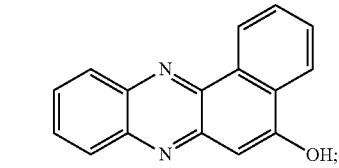

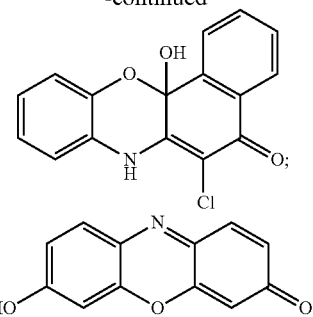
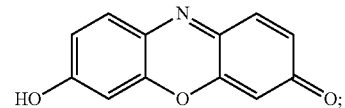
and pharmaceutically acceptable salts thereof.
* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: PCR Primer

<400> SEQUENCE: 1
cgattactga agctgcctcg a                                              21

<210> SEQ ID NO 2
<211> LENGTH: 21
<212> TYPE: DNA
<213> ORGANISM: Artificial Sequence
<220> FEATURE:
<223> OTHER INFORMATION: PCR Primer

<400> SEQUENCE: 2
ggttttttgg caaggaacca c                                              21

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
tccttgccaa aaaaccctgg                                                20

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
atgcccacca ccttctcttc a                                              21

<210> SEQ ID NO 5
<211> LENGTH: 19
<212> TYPE: DNA
<213> ORGANISM: Artificial Sequence
<220> FEATURE:
<223> OTHER INFORMATION: PCR Primer
```

```
<400> SEQUENCE: 5
gaaggtgaag gtcggagtc                                                 19

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
gaagatggtg atgggatttc                                                20
```